US008859717B2

(12) United States Patent
Ie et al.

(10) Patent No.: US 8,859,717 B2
(45) **Date of Patent: *Oct. 14, 2014**

(54) NITROGEN-CONTAINING FUSED RING COMPOUND, NITROGEN-CONTAINING FUSED RING POLYMER, ORGANIC THIN FILM, AND ORGANIC THIN FILM ELEMENT

(75) Inventors: Yutaka Ie, Suita (JP); Masashi Ueta, Suita (JP); Yoshio Aso, Suita (JP); Masato Ueda, Tsukuba (JP)

(73) Assignees: Sumitomo Chemical Company, Limited, Tokyo (JP); Osaka University, Osaka (JP)

( * ) Notice: Subject to any disclaimer, the term of this patent is extended or adjusted under 35 U.S.C. 154(b) by 123 days.

This patent is subject to a terminal disclaimer.

(21) Appl. No.: 13/582,246

(22) PCT Filed: Mar. 3, 2011

(86) PCT No.: PCT/JP2011/054924

§ 371 (c)(1), (2), (4) Date: Oct. 31, 2012

(87) PCT Pub. No.: WO2011/108646

PCT Pub. Date: Sep. 9, 2011

(65) Prior Publication Data

US 2013/0041123 A1 Feb. 14, 2013

(30) Foreign Application Priority Data

Mar. 4, 2010 (JP) ................................ 2010-047852
Nov. 24, 2010 (JP) ................................ 2010-261575

(51) Int. Cl.

*C08G 75/00* (2006.01)
*C07D 513/14* (2006.01)
*C07D 513/04* (2006.01)
*H01L 51/00* (2006.01)
*H01L 51/05* (2006.01)

(52) U.S. Cl.

CPC .......... *H01L 51/0036* (2013.01); *C07D 513/14* (2013.01); *H01L 51/0545* (2013.01); *Y02E 10/549* (2013.01); *C07D 513/04* (2013.01); *H01L 51/0541* (2013.01)

USPC ............ 528/378; 528/380; 526/257; 548/148

(58) Field of Classification Search

USPC ............ 528/377, 378, 380; 526/257; 548/148
See application file for complete search history.

(56) References Cited

U.S. PATENT DOCUMENTS

2004/0004215 A1 1/2004 Iechi et al.
2004/0186266 A1 9/2004 Jiang et al.

(Continued)

FOREIGN PATENT DOCUMENTS

JP 5-110069 A 4/1993
JP 2004-006476 A 1/2004

(Continued)

OTHER PUBLICATIONS

International Preliminary Report on Patentability and Written Opinion dated Oct. 11, 2012 in International Application No. PCT/JP2011/054924 to Sumitomo Chemical Co., Ltd.
Glinzer, Otto et al., "Mass spectrometry of bisanellated thiophenediones as model sustances for oxidation products of sulfur compounds in high-boiling crude oil fractions", Fresenius Zeitschrift fuer Analytische Chemie, 1983, p. 505-9, vol. 315, No. 6, Table 1, Compound No. 7.

*Primary Examiner* — Shane Fang
(74) *Attorney, Agent, or Firm* — Sughrue Mion, PLLC

(57) ABSTRACT

Nitrogen-containing fused ring compound having at least one structural unit selected from the group consisting of a structural unit represented by the formula (1-1) and a structural unit represented by the formula (1-2).

28 Claims, 12 Drawing Sheets

(56) References Cited

U.S. PATENT DOCUMENTS

| | | | | |
|---|---|---|---|---|
| 2004/0230021 | A1 | 11/2004 | Giles et al. | |
| 2009/0315022 | A1 | 12/2009 | Morishita et al. | |
| 2010/0171102 | A1* | 7/2010 | Ie et al. | 257/40 |
| 2010/0301314 | A1 | 12/2010 | Aso et al. | |
| 2011/0065895 | A1* | 3/2011 | Miura et al. | 528/380 |
| 2011/0087034 | A1 | 4/2011 | Miyata et al. | |
| 2011/0284827 | A1 | 11/2011 | Morishita et al. | |

FOREIGN PATENT DOCUMENTS

| | | | |
|---|---|---|---|
| JP | 2009-215278 | A | 9/2009 |
| WO | 2009-069717 | A1 | 6/2009 |
| WO | 2009-099070 | A1 | 8/2009 |
| WO | 2010-064655 | A1 | 6/2010 |

* cited by examiner

NITROGEN-CONTAINING FUSED RING COMPOUND, NITROGEN-CONTAINING FUSED RING POLYMER, ORGANIC THIN FILM, AND ORGANIC THIN FILM ELEMENT

CROSS REFERENCE TO RELATED APPLICATIONS

This application is a National Stage of International Application No. PCT/JP2011/054924 filed Mar. 3, 2011, claiming priority based on Japanese Patent Application Nos. 2010-047852 filed Mar. 4, 2010 and JP 2010-261575 filed Nov. 24, 2010, the contents of all of which are incorporated herein by reference in their entirety.

TECHNICAL FIELD

The present invention relates to a nitrogen-containing fused ring compound, a nitrogen-containing fused ring polymer, an organic thin film and an organic thin film device.

BACKGROUND ART

Thin films containing organic materials having electron transport properties or hole transport properties are expected to be applied to organic thin film devices such as organic thin film transistors, organic solar cells and optical sensors. Development of various organic n-type semiconductors has been discussed, because it is difficult to provide organic n-type semiconductors (having electron transport properties) as compared with organic p-type semiconductors (having hole transport properties).

In recent years, Patent Literature 1 discloses compounds having a fluoroalkyl group introduced into a thiophene ring as thin film transistor materials, for example.

Patent Literature 2 discloses monomers, oligomers and polymers containing at least one dithienothiophene group and at least one arylene or heteroarylene group as charge transfer materials, for example.

CITATION LIST

Patent Literature

Patent Literature 1: U.S. Patent Application Laid-Open No. 2004/186266

Patent Literature 2: U.S. Patent Application Laid-Open No. 2004/230021

SUMMARY OF INVENTION

Technical Problem

However, even the aforementioned known materials do not have sufficient performance as organic n-type semiconductors, and there is a need for organic n-type semiconductors having further improved electron transport properties.

An object of the present invention is to provide novel compounds and novel polymers that can be used as organic n-type semiconductors having high electron transport properties. Another object of the present invention is to provide organic thin films comprising the novel compounds and/or the novel polymers, and organic thin film devices comprising the organic thin films.

Solution to Problem

The present invention provides a nitrogen-containing fused ring compound having at least one structural unit selected from the group consisting of a structural unit represented by the formula (1-1) and a structural unit represented by the formula (1-2):

[Chemical Formula 1]

(1-1)

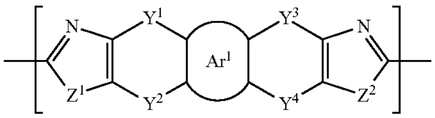

(1-2)

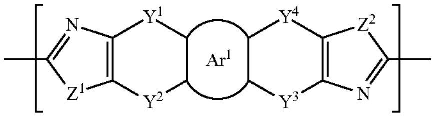

wherein $Ar^1$ represents an aromatic ring having 4 or more carbon atoms which may have a substituent, either one of $Y^1$ and $Y^2$ represents a group represented by $—C(═X^1)—$ and the other represents a single bond, either one of $Y^3$ and $Y^4$ represents a group represented by $—C(═X^2)—$ and the other represents a single bond, $X^1$ and $X^2$ each independently represent an oxygen atom, a sulfur atom or a group represented by $═C(A^1)_2$ (wherein $A^1$ represents a hydrogen atom, a halogen atom or a monovalent group, and two $A^1$s may be identical to or different from each other), and $Z^1$ and $Z^2$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5):

[Chemical Formula 2]

(a-1)

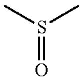

(a-2)

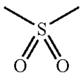

(a-3)

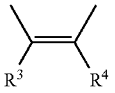

(a-4)

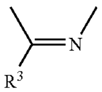

(a-5)

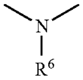

wherein $R^3$, $R^4$, $R^5$ and $R^6$ each independently represent a hydrogen atom, a halogen atom or a monovalent group, and $R^3$ and $R^4$ may be bonded to each other to form a ring.

The group represented by the formula (a-3) and the group represented by the formula (a-4) may be bonded in any of the two bonding arrangements left-right reversed.

The nitrogen-containing fused ring compounds of the present invention have high π-conjugation planarity between the rings and can have a sufficiently low lowest unoccupied molecular orbital (LUMO) due to introduction of the nitrogen-containing fused ring. For this reason, the compounds can be used as organic n-type semiconductors having high electron transport properties. The nitrogen-containing fused ring compounds of the present invention are highly soluble in organic solvents. Therefore, thin films are easily formed using them, and organic thin film devices having high performance can be manufactured.

The nitrogen-containing fused ring compounds of the present invention are chemically stable and have high environmental stability (i.e., stability against air or water). Thus, organic thin film devices having stable performance even in the atmosphere can be manufactured by forming thin films using them.

The above $Z^1$ and $Z^2$ are preferably sulfur atoms. Such nitrogen-containing fused ring compounds can have an electronic state suitable for electron transport, and have further improved electron transport properties, by the interaction between the sulfur atoms and the nitrogen atoms forming rings together with the sulfur atoms.

The above $X^1$ and $X^2$ are preferably oxygen atoms. Such nitrogen-containing fused ring compounds can have an even lower LUMO, and in a solid state, easily interact with heteroatoms in the adjacent molecules, thus increasing intermolecular interaction and further improving electron transport properties.

The above $Ar^1$ is preferably a benzene ring or a thiophene ring. Such nitrogen-containing fused ring compounds are easily π-conjugated and have improved π-conjugation planarity, so that the molecules are easily aligned.

In the nitrogen-containing fused ring compounds of the present invention, the structural unit represented by the formula (1-1) is preferably a structural unit represented by the formula (2-1), and the structural unit represented by the formula (1-2) is preferably a structural unit represented by the formula (2-2):

[Chemical Formula 3]

(2-1)

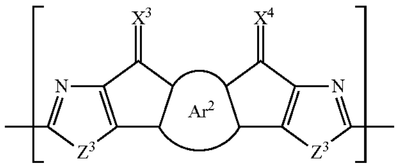

(2-2)

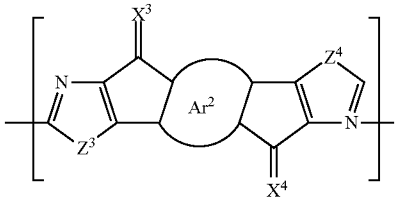

wherein $Ar^2$ represents an aromatic ring having 4 or more carbon atoms which may have a substituent, $X^3$ and $X^4$ each independently represent an oxygen atom, a sulfur atom or a group represented by $=C(A^2)_2$ (wherein $A^2$ represents a hydrogen atom, a halogen atom or a monovalent group, and two $A^2$s may be identical to or different from each other, provided that at least one of the two $A^2$s represents a cyano group, a nitro group, an acyl group, an alkoxycarbonyl group, a carboxyl group, a hydroxy group or a halogen atom), and $Z^3$ and $Z^4$ each independently represent an oxygen atom, a sulfur atom, a selenium atom, a tellurium atom, a group represented by the formula (b-1), a group represented by the formula (b-2), a group represented by the formula (b-3), a group represented by the formula (b-4) or a group represented by the formula (b-5):

[Chemical Formula 4]

(b-1)

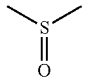

(b-2)

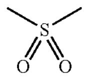

(b-3)

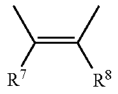

(b-4)

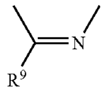

(b-5)

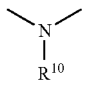

wherein $R^7$, $R^8$, $R^9$ and $R^{10}$ each independently represent a hydrogen atom, a halogen atom or a monovalent group, and $R^7$ and $R^8$ may be bonded to each other to form a ring.

The group represented by the formula (b-3) and the group represented by the formula (b-4) may be bonded in any of the two bonding arrangements left-right reversed.

The above $Z^3$ and $Z^4$ are preferably sulfur atoms. Such nitrogen-containing fused ring compounds can have an electronic state suitable for electron transport, and have further improved electron transport properties, by the interaction between the sulfur atoms and the nitrogen atoms forming rings together with the sulfur atoms.

The above $X^3$ and $X^4$ are preferably oxygen atoms. Such nitrogen-containing fused ring compounds can have an even lower LUMO, and in a solid state, easily interact with heteroatoms in the adjacent molecules, thus increasing intermolecular interaction and further improving electron transport properties.

The above $Ar^2$ is preferably a benzene ring or a thiophene ring. Such nitrogen-containing fused ring compounds are easily π-conjugated and have improved π-conjugation planarity, so that the molecules are easily aligned.

In the nitrogen-containing fused ring compounds of the present invention, the structural unit represented by the formula (1-1) and the structural unit represented by the formula (1-2) preferably have line symmetry or point symmetry, and more preferably have point symmetry. In this case, the number of intermolecular interaction sites can be expected to grow, intermolecular interaction is increased, and the molecules are easily aligned, thus further improving electron transport properties.

The nitrogen-containing fused ring compounds of the present invention are preferably nitrogen-containing fused ring compounds in which the structural unit represented by the formula (1-1) is a structural unit represented by the formula (3-1), and the structural unit represented by the formula (1-2) is a structural unit represented by the formula (3-2). Such nitrogen-containing fused ring compounds are particularly superior in the aforementioned characteristics.

[Chemical Formula 5]

(3-1)

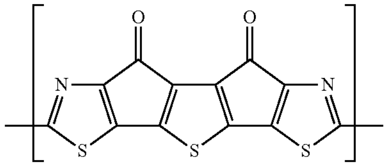

(3-2)

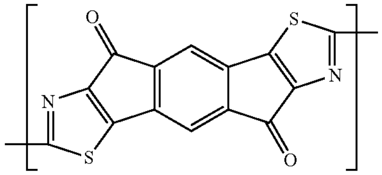

The present invention also provides a nitrogen-containing fused ring polymer having a plurality of structural units selected from the group consisting of structural units represented by the formula (1-1) and structural units represented by the formula (1-2). Here, the plurality of structural units possessed by the nitrogen-containing fused ring polymer may be identical to or different from each other.

Specifically, the present invention provides a nitrogen-containing fused ring polymer having a plurality of structural units represented by the formula (1-1), or having a plurality of structural units represented by the formula (1-2), or having at least one group represented by the formula (1-1) and at least one group represented by the formula (1-2). As described above, the plurality of structural units possessed by the nitrogen-containing fused ring polymer may be identical to or different from each other.

The nitrogen-containing fused ring polymers of the present invention have high π-conjugation planarity between the rings in the above structural units and can have a sufficiently low LUMO due to introduction of a plurality of the nitrogen-containing fused rings. For this reason, the polymers can be used as organic n-type semiconductors having high electron transport properties. The nitrogen-containing fused ring polymers of the present invention are chemically stable and highly soluble in organic solvents. Therefore, organic thin film devices having high performance can be manufactured by forming thin films using them.

The nitrogen-containing fused ring polymers of the present invention have high environmental stability. Thus, organic thin film devices having stable performance even in the atmosphere can be manufactured by forming thin films using them.

In the nitrogen-containing fused ring polymers of the present invention, the above $Z^1$ and $Z^2$ are preferably sulfur atoms. Such nitrogen-containing fused ring polymers can have an electronic state suitable for electron transport, and have further improved electron transport properties, by the interaction between the sulfur atoms and the nitrogen atoms forming rings together with the sulfur atoms.

In the nitrogen-containing fused ring polymers of the present invention, the above $X^1$ and $X^2$ are preferably oxygen atoms. Such nitrogen-containing fused ring polymers can have an even lower LUMO, and in a solid state, easily interact with heteroatoms in the adjacent molecules, thus increasing intermolecular interaction and further improving electron transport properties.

In the nitrogen-containing fused ring polymers of the present invention, the structural unit represented by the formula (1-1) is preferably a structural unit represented by the formula (2-1), and the structural unit represented by the formula (1-2) is preferably a structural unit represented by the formula (2-2).

In the nitrogen-containing fused ring polymers of the present invention, the above $Z^3$ and $Z^4$ are preferably sulfur atoms. Such nitrogen-containing fused ring polymers can have an electronic state suitable for electron transport, and have further improved electron transport properties, by the interaction between the sulfur atoms and the nitrogen atoms forming rings together with the sulfur atoms.

In the nitrogen-containing fused ring polymers of the present invention, the above $X^3$ and $X^4$ are preferably oxygen atoms. Such nitrogen-containing fused ring polymers can have an even lower LUMO, and in a solid state, easily interact with heteroatoms in the adjacent molecules, thus increasing intermolecular interaction and further improving electron transport properties.

In the nitrogen-containing fused ring polymers of the present invention, the above aromatic ring is preferably a benzene ring or a thiophene ring. Such nitrogen-containing fused ring polymers are easily π-conjugated and have improved π-conjugation planarity, so that the molecules are easily aligned.

In the nitrogen-containing fused ring polymers of the present invention, the structural unit represented by the formula (1-1) and the structural unit represented by the formula (1-2) preferably have line symmetry or point symmetry, and more preferably have point symmetry. In this case, the number of intermolecular interaction sites can be expected to grow, intermolecular interaction is increased, and the molecules are easily aligned, thus further improving electron transport properties.

The nitrogen-containing fused ring polymers of the present invention may further have a structural unit represented by the formula (4). Solubility or mechanical, thermal or electronic characteristics can be more widely changed by providing such a structural unit.

[Chemical Formula 6]

$$-\!\!\left(Ar^3\right)\!\!- \qquad (4)$$

In the formula, $Ar^3$ represents an arylene group which may have a substituent, or a heterocyclic group which may have a substituent.

The nitrogen-containing fused ring polymers of the present invention may further have a structural unit represented by the formula (5):

[Chemical Formula 7]

(5)

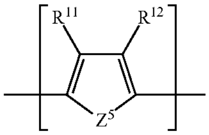

wherein $R^{11}$ and $R^{12}$ each independently represent a hydrogen atom, a halogen atom or a monovalent group, and $Z^5$ represents an oxygen atom, a sulfur atom, a selenium atom, a tellurium atom, a group represented by the formula (c-1), a group represented by the formula (c-2), a group represented by the formula (c-3), a group represented by the formula (c-4) or a group represented by the formula (c-5):

[Chemical Formula 8]

(c-1)

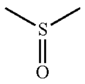

(c-2)

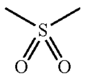

(c-3)

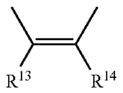

(c-4)

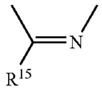

(c-5)

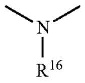

wherein $R^{13}$, $R^{14}$, $R^{15}$ and $R^{16}$ each independently represent a hydrogen atom, a halogen atom or a monovalent group, and $R^{13}$ and $R^{14}$ may be bonded to each other to form a ring.

The group represented by the formula (c-3) and the group represented by the formula (c-4) may be bonded in any of the two bonding arrangements left-right reversed.

The above $Z^5$ is preferably a sulfur atom. The nitrogen-containing fused ring polymers having such a structural unit can have a stable quinoid structure, and therefore have even higher electron transport properties.

The present invention also provides an organic thin film comprising at least one selected from the group consisting of the nitrogen-containing fused ring compound of the present invention and the nitrogen-containing fused ring polymer of the present invention. Such organic thin films comprise at least the nitrogen-containing fused ring compounds or the nitrogen-containing fused ring polymers, and thus have a sufficiently low LUMO and high electron transport properties.

The present invention also provides an organic thin film device, an organic thin film transistor and an organic solar cell, comprising the organic thin film of the present invention. Such organic thin film devices, organic thin film transistors and organic solar cells comprise the organic thin films of the present invention, and the organic thin films can efficiently transport charges injected from electrodes, charges generated by light absorption, and the like. Therefore, the organic thin film devices of the present invention have high performance, the organic thin film transistors of the present invention have high electron mobility, and the organic solar cells of the present invention have high conversion efficiency.

Advantageous Effects of Invention

The present invention can provide novel nitrogen-containing fused ring compounds and novel nitrogen-containing fused ring polymers that can be used as organic n-type semiconductors having high electron transport properties. The present invention can also provide organic thin films comprising the nitrogen-containing fused ring compounds and/or the nitrogen-containing fused ring polymers, and organic thin film devices comprising the organic thin films.

DESCRIPTION OF EMBODIMENTS

Figure 1:
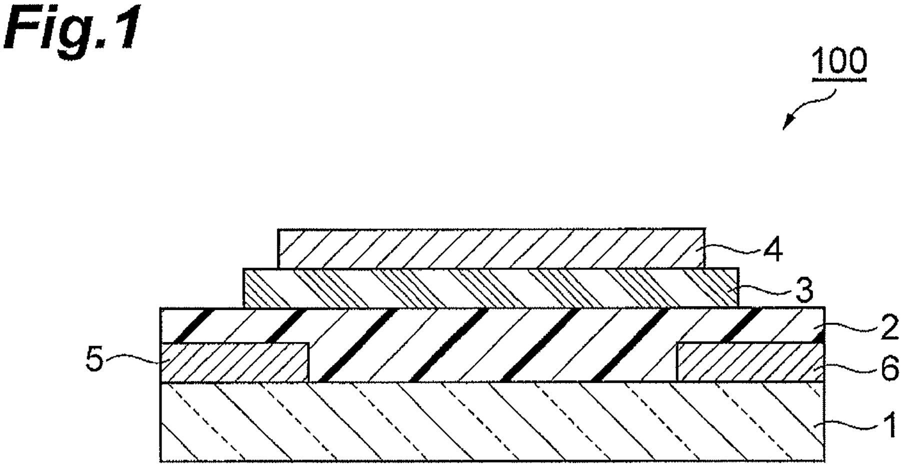
FIG. 1 is a schematic cross-sectional view of an organic thin film transistor according to a first embodiment.

Preferred embodiments of the present invention will be described in detail below optionally with reference to drawings. In the drawings, identical symbols are given to identical elements, and the repeated description is omitted. Positional relations such as top-bottom and left-right relations are based on positional relations shown in the drawings unless otherwise noted. Further, dimensional ratios are not limited to those shown in the drawings.

The nitrogen-containing fused ring compounds of the present embodiment have at least one structural unit selected from the group consisting of a structural unit represented by the formula (1-1) and a structural unit represented by the formula (1-2).

The nitrogen-containing fused ring compounds of the present embodiment have such a structural unit, and thus have high π-conjugation planarity between the rings and can have a sufficiently low LUMO. For this reason, the compounds can be used as organic n-type semiconductors having high electron transport properties. The nitrogen-containing fused ring compounds of the present embodiment are chemically stable and highly soluble in organic solvents. Therefore, organic thin film devices having high performance can be manufactured by forming thin films using them.

The nitrogen-containing fused ring compounds of the present embodiment have high environmental stability (i.e., stability against air or water). Thus, organic thin film devices having stable performance even in a normal atmosphere can be manufactured by forming thin films using them.

$Ar^1$ represents an aromatic ring having 4 or more carbon atoms which may have a substituent. Examples of the aromatic ring include benzenoid aromatic rings and heteroaromatic rings. The aromatic ring may be a single ring or a fused ring. The aromatic ring is preferably a single ring or a fused ring in which 2 to 5 rings are fused, more preferably a single ring or a fused ring in which two rings are fused, still more preferably a single ring, because this enables high solubility and easy manufacture.

Benzenoid aromatic rings include benzene, naphthalene, anthracene, fluorene, pyrene and perylene. Benzene or naphthalene is preferred, and benzene is more preferred. Heteroaromatic rings include pyridine, thiophene, thienothiophene, dithienothiophene, benzothiophene, benzodithiophene, dibenzothiophene, pyrrole, quinoline and indole. Thiophene, thienothiophene or pyridine is preferred, and thiophene is more preferred.

The aromatic ring represented by $Ar^1$ may have a substituent. The substituent is preferably a substituent formed by 20 or less atoms, more preferably a substituent formed by 17 or less atoms. Examples of the substituent include alkyl groups such as a methyl group, an ethyl group, an n-propyl group, an isopropyl group and a sec-propyl group (where the alkyl groups have preferably 1 to 12, more preferably 1 to 10, carbon atoms); alkoxy groups such as a methoxy group, an ethoxy group, an n-propyloxy group, an isopropyloxy group and a sec-propyloxy group (where the alkoxy groups have preferably 1 to 12, more preferably 1 to 10, carbon atoms); aryl groups such as a phenyl group and a naphthyl group; halogen atoms such as a fluorine atom, a chlorine atom and a bromine atom; a nitro group; and a cyano group.

The aryl group herein refers to a remaining atomic group obtained by removing one hydrogen atom from an aromatic hydrocarbon compound. Examples of the aromatic hydrocarbon compound include benzene, naphthalene, anthracene, phenanthrene, naphthacene, fluorene, benzofluorene, pyrene and perylene.

Either one of $Y^1$ and $Y^2$ represents a group represented by $—C(=X^1)—$ and the other represents a single bond. Either one of $Y^3$ and $Y^4$ represents a group represented by $—C(=X^2)—$ and the other represents a single bond. In the present embodiment, it is preferred that $Y^1$ of $Y^1$ and $Y^2$ be a group represented by $—C(=X^1)—$. It is also preferred that $Y^3$ of $Y^3$ and $Y^4$ be a group represented by $—C(=X^2)—$.

$X^1$ and $X^2$ each independently represent an oxygen atom, a sulfur atom or a group represented by $=C(A^1)_2$. $X^1$ and $X^2$ are each preferably an oxygen atom or a group represented by $=C(A^1)_2$, more preferably an oxygen atom. $X^1$ and $X^2$ are preferably the same groups, because this enables easy manufacture.

$A^1$ represents a hydrogen atom, a halogen atom or a monovalent group. In the group represented by $=C(A^1)_2$, two $A^1$s may be identical to or different from each other. It is preferred that at least one of the two $A^1$s be an electron-accepting group, and it is more preferred that both of the two $A^1$s be electron-accepting groups, because this can allow the LUMO to be even lower.

At least one of the two $A^1$s is preferably a cyano group, a nitro group, an acyl group, an alkoxycarbonyl group (where the alkoxycarbonyl group has preferably 2 to 13, more preferably 2 to 11, carbon atoms), a carboxyl group, a hydroxy group or a halogen atom, more preferably a cyano group, a nitro group or a halogen atom, still more preferably a cyano group.

Both of the two $A^1$s are preferably a cyano group, a nitro group, an acyl group, an alkoxycarbonyl group (where the alkoxycarbonyl group has preferably 2 to 13, more preferably 2 to 11, carbon atoms), a carboxyl group, a hydroxy group or a halogen atom, more preferably a cyano group, a nitro group or a halogen atom, still more preferably a cyano group.

The acyl group herein refers to a group represented by $—C(=O)—R^{17}$. Here, $R^{17}$ represents a hydrogen atom, an alkyl group or an aryl group. The alkyl group in $R^{17}$ has preferably 1 to 12, more preferably 1 to 10, carbon atoms. The acyl group where $R^{17}$ is a hydrogen atom is also called formyl group, and the acyl group where $R^{17}$ is an alkyl group is also called alkanoyl group.

$Z^1$ and $Z^2$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5). $Z^1$ and $Z^2$ are each preferably an oxygen atom, a sulfur atom, a selenium atom, a group represented by the formula (a-3), a group represented by the formula (a-4) or a group represented by the formula (a-5), more preferably a sulfur atom or a group represented by the formula (a-3).

$R^3$, $R^4$, $R^5$ and $R^6$ each independently represent a hydrogen atom, a halogen atom or a monovalent group, and $R^3$ and $R^4$ may be bonded to each other to form a ring.

The monovalent group in $R^3$, $R^4$, $R^5$ and $R^6$ may be a linear or branched chain group, or a cyclic group. Here, the chain group refers to a group not having a cyclic structure. The cyclic group refers to a group having a cyclic structure. The cyclic structure may be a single ring or a fused ring, may be a carbocycle or a heterocycle, and may be saturated or unsaturated. The carbocycle is a cyclic structure composed of carbon atoms, and the heterocycle is a cyclic structure having an atom other than carbon atoms (a heteroatom). The monovalent group in $R^3$, $R^4$, $R^5$ and $R^6$ may be an electron-donating group or an electron-accepting group.

Examples of the monovalent group in $R^3$, $R^4$, $R^5$ and $R^6$ include a chain group having 1 to 20 carbon atoms, and a cyclic group having 3 to 60 atoms forming the ring (hereinafter optionally called "ring-forming atoms").

The chain group is preferably an alkyl group (where the alkyl group has preferably 1 to 12, more preferably 1 to 10, carbon atoms), an unsaturated hydrocarbon group (where the unsaturated hydrocarbon group has preferably 1 to 12, more preferably 1 to 10, carbon atoms), a hydroxy group, an alkoxy group (where the alkoxy group has preferably 1 to 12, more preferably 1 to 10, carbon atoms), an alkanoyloxy group (where the alkanoyloxy group has preferably 2 to 13, more preferably 2 to 11, carbon atoms), an amino group, a hydroxyamino group, an alkylamino group (where the alkyl group in the alkylamino group has preferably 1 to 12, more preferably 1 to 10, carbon atoms), a dialkylamino group (where the alkyl group in the dialkylamino group has preferably 1 to 12, more preferably 1 to 10, carbon atoms), an alkanoylamino group (where the alkanoylamino group has preferably 2 to 13, more preferably 2 to 11, carbon atoms), a cyano group, a nitro group, a sulfo group, an alkylsulfonyl group (where the alkyl group in the alkylsulfonyl group has preferably 1 to 12, more preferably 1 to 10, carbon atoms), a sulfamoyl group, an alkylsulfamoyl group (where the alkyl group in the alkylsulfamoyl group has preferably 1 to 12, more preferably 1 to 10, carbon atoms), a carboxyl group, a carbamoyl group, an alkylcarbamoyl group (where the alkyl group in the alkylcarbamoyl group has preferably 1 to 12, more preferably 1 to 10, carbon atoms), a formyl group, an alkanoyl group (where the alkanoyl group has preferably 2 to 13, more preferably 2 to 11, carbon atoms) or an alkoxycarbonyl group (where the alkoxycarbonyl group has preferably 2 to 13, more preferably 2 to 11, carbon atoms), and is also preferably a group in which some or all of the hydrogen atoms in such a group are replaced with a halogen atom(s).

Examples of the cyclic group include an aryl group and a cycloalkyl group (where the cycloalkyl group has preferably 3 to 12, more preferably 3 to 10, carbon atoms). Further examples of the cyclic group include groups represented by the following formulas.

[Chemical Formula 9]

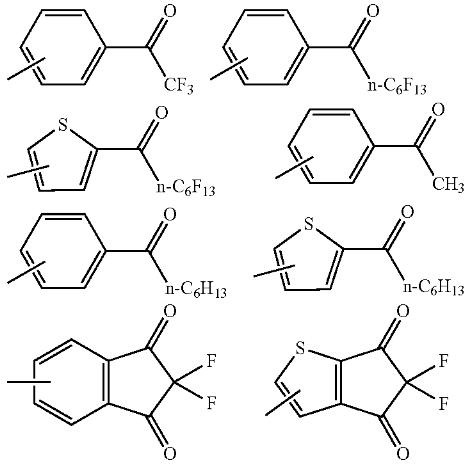

The monovalent group in $R^3$, $R^4$, $R^5$ and $R^6$ is preferably a hydrogen atom, a halogen atom, an alkyl group (where the alkyl group has preferably 1 to 12, more preferably 1 to 10, carbon atoms), an alkoxy group (where the alkoxy group has preferably 1 to 12, more preferably 1 to 10, carbon atoms) or an aryl group, more preferably a hydrogen atom, an alkyl group or an aryl group.

The monovalent group in $R^3$, $R^4$, $R^5$ and $R^6$ may be a group prepared by replacing some or all of the hydrogen atoms in the above group with a substituent(s). Here, the substituent is preferably a substituent formed by 20 or less atoms, more preferably a substituent formed by 17 or less atoms. Specific examples include alkyl groups such as a methyl group, an ethyl group, an n-propyl group, an isopropyl group and a sec-propyl group (preferably an alkyl group having 1 to 12 carbon atoms, more preferably an alkyl group having 1 to 10 carbon atoms); alkoxy groups such as a methoxy group, an ethoxy group, an n-propyloxy group, an isopropyloxy group and a sec-propyloxy group (preferably an alkoxy group having 1 to 12 carbon atoms, more preferably an alkoxy group having 1 to 10 carbon atoms); aryl groups such as a phenyl group and a naphthyl group; halogen atoms such as a fluorine atom, a chlorine atom and a bromine atom; a nitro group; and a cyano group.

Examples of the halogen atom herein include a fluorine atom, a chlorine atom, a bromine atom and an iodine atom.

The alkyl group herein may be linear or branched. Examples of the alkyl group include a methyl group, an ethyl group, an n-propyl group, an isopropyl group, a sec-propyl group, an n-butyl group, an isobutyl group, a sec-butyl group and a tert-butyl group. The alkyl group has preferably 1 to 12, more preferably 1 to 10, carbon atoms. The same groups as described above can be provided herein as examples of the alkyl group in the group having an alkyl group in its structure (such as an alkoxy group, an alkylamino group or an alkoxycarbonyl group).

Examples of the unsaturated hydrocarbon group include a vinyl group, a 1-propenyl group, an allyl group, a propargyl group, an isopropenyl group, a 1-butenyl group and a 2-butenyl group. Among these, a vinyl group is preferred. The unsaturated hydrocarbon group has preferably 1 to 12, more preferably 1 to 10, carbon atoms.

Examples of the alkanoyl group include an acetyl group, a propionyl group, an isobutyryl group, a valeryl group and an isovaleryl group. The same groups can be provided as examples of the alkanoyl group in the group having an alkanoyl group in its structure (such as an alkanoyloxy group or an alkanoylamino group). Preferred alkanoyl groups include an acetyl group.

Examples of the nitrogen-containing fused ring compounds of the present embodiment include compounds represented by the formula (6-1) or (6-2).

[Chemical Formula 10]

(6-1)

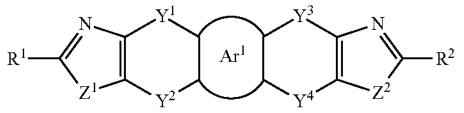

(6-2)

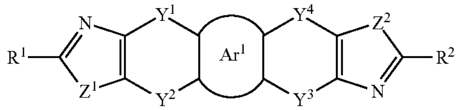

$Ar^1$, $Y^1$, $Y^2$, $Y^3$, $Y^4$, $Z^1$ and $Z^2$ are as described above, and $R^1$ and $R^2$ each independently represent a hydrogen atom, a halogen atom or a monovalent group. The same monovalent groups as in $R^3$, $R^4$, $R^5$ and $R^6$ can be provided as examples of the monovalent group in $R^1$ and $R^2$.

The monovalent groups in $R^1$ and $R^2$ are preferably groups represented by the following formulas.

[Chemical Formula 11]

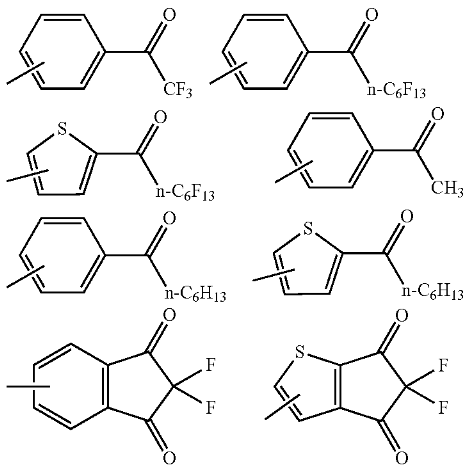

The monovalent group in $R^1$ and $R^2$ is preferably a linear or branched chain group, more preferably a linear or branched alkyl group or a linear or branched alkoxy group, still more preferably a linear or branched alkyl group, in terms of solubility in organic solvents of the nitrogen-containing fused ring compounds.

The monovalent group in $R^1$ and $R^2$ is preferably a group having at least one fluorine atom, or a group having at least one carbonyl group, more preferably a group having at least one fluorine atom and at least one carbonyl group. Such a group further lowers the LUMO and further improves solubility in organic solvents.

The monovalent group in $R^1$ and $R^2$ is preferably a fluoroalkyl group (where the fluoroalkyl group has preferably 1 to 12, more preferably 1 to 10, carbon atoms), a fluoroalkoxy group (where the fluoroalkoxy group has preferably 1 to 12, more preferably 1 to 10, carbon atoms), a fluoroaryl group, a group having an α-fluorocarbonyl structure (a structure represented by —C(═O)—CF<), an aryl group in which at least one hydrogen atom is replaced with a fluoroalkyl group, an aryl group in which at least one hydrogen atom is replaced with a fluoroalkoxy group, an aryl group in which at least one hydrogen atom is replaced with a group having an α-fluorocarbonyl structure, an aryl group fused with a cyclic structure having an α-fluorocarbonyl structure, a heterocyclic group in which at least one hydrogen atom is replaced with a fluoroalkyl group, a heterocyclic group in which at least one hydrogen atom is replaced with a fluoroalkoxy group, a heterocyclic group in which at least one hydrogen atom is replaced with a group having an α-fluorocarbonyl structure, or a heterocyclic group fused with a cyclic structure having an α-fluorocarbonyl structure in terms of electron transport properties.

The monovalent group in $R^1$ and $R^2$ is more preferably a fluoroalkyl group, a fluoroalkoxy group, a fluoroaryl group, a group having an α-fluorocarbonyl structure, an aryl group in which at least one hydrogen atom is replaced with a fluoroalkyl group, an aryl group in which at least one hydrogen atom is replaced with a fluoroalkoxy group, a heterocyclic group in which at least one hydrogen atom is replaced with a fluoroalkyl group, a heterocyclic group in which at least one hydrogen atom is replaced with a fluoroalkoxy group, a heterocyclic group in which at least one hydrogen atom is replaced with a group having an α-fluorocarbonyl structure, or a heterocyclic group fused with a cyclic structure having an α-fluorocarbonyl structure.

The monovalent group in $R^1$ and $R^2$ is still more preferably a heterocyclic group in which at least one hydrogen atom is replaced with a fluoroalkyl group, a heterocyclic group in which at least one hydrogen atom is replaced with a fluoroalkoxy group, a heterocyclic group in which at least one hydrogen atom is replaced with a group having an a-fluorocarbonyl structure, or a heterocyclic group fused with a cyclic structure having an α-fluorocarbonyl structure. Electron transport properties of the nitrogen-containing fused ring compounds are further improved when both $R^1$ and $R^2$ are such groups.

The monovalent heterocyclic group herein refers to a remaining atomic group obtained by removing one hydrogen atom from a heterocyclic compound. Here, the heterocyclic compound refers to an organic compound having a cyclic structure, which has a heteroatom such as an oxygen atom, a sulfur atom, a nitrogen atom, a phosphorus atom, a boron atom or a silicon atom as an atom forming the ring. Examples of the heterocyclic compound include thiophene; compounds prepared by fusing 2 to 6 thiophene rings such as thienothiophene and dithienothiophene; benzothiophene; benzodithiophene; dibenzothiophene; thiazole; pyrrole; pyridine; and pyrimidine. The monovalent heterocyclic group is preferably a group having 3 to 60 carbon atoms forming the ring, more preferably a group having 3 to 20 carbon atoms forming the ring.

Also, the monovalent heterocyclic group is preferably a remaining atomic group obtained by removing one hydrogen atom from thiophene, a compound prepared by fusing 2 to 6 thiophene rings such as thienothiophene, benzothiophene, benzodithiophene, dibenzothiophene or thiazole.

The monovalent heterocyclic group may have a substituent. Examples of the substituent include a halogen atom, an alkyl group (where the alkyl group has preferably 1 to 12, more preferably 1 to 10, carbon atoms), an unsaturated hydrocarbon group (where the unsaturated hydrocarbon group has preferably 1 to 12, more preferably 1 to 10, carbon atoms), an aryl group, an alkoxy group (where the alkoxy group has preferably 1 to 12, more preferably 1 to 10, carbon atoms), an aryloxy group, a monovalent heterocyclic group, an amino group, a nitro group and a cyano group.

The monovalent group in $R^1$ and $R^2$ may be a polymerizable group. Such nitrogen-containing fused ring compounds can be suitably used as raw material compounds for synthesizing the nitrogen-containing fused ring polymers described later (which may be called precursors of nitrogen-containing fused ring polymers). $R^1$ and $R^2$ are each preferably a hydrogen atom, a halogen atom or a polymerizable group when the compounds are used as raw material compounds for synthesizing the nitrogen-containing fused ring polymers.

The polymerizable group herein refers to a group that can cause polymerization reaction (e.g., addition polymerization reaction or condensation polymerization reaction). Examples include an alkyl sulfonate group (where the alkyl group in the alkyl sulfonate group has preferably 1 to 12, more preferably 1 to 10, carbon atoms), an aryl sulfonate group, an arylalkyl sulfonate group (where the alkyl group in the arylalkyl sulfonate group has preferably 1 to 12, more preferably 1 to 10, carbon atoms), an alkylstannyl group (where the alkyl group in the alkylstannyl group has preferably 1 to 12, more preferably 1 to 10, carbon atoms), an arylstannyl group, an arylalkylstannyl group (where the alkyl group in the arylalkylstannyl group has preferably 1 to 12, more preferably 1 to 10, carbon atoms), a borate residue, a sulfonium methyl group, a phosphonium methyl group, a phosphonate methyl group, a monohalogenated methyl group, a boric acid residue (a group represented by $—B(OH)_2$), a formyl group and a vinyl group.

$R^1$ and $R^2$ are each preferably a halogen atom, an alkylstannyl group or a borate residue, because synthesis is easily performed when the compounds are used as raw material compounds for synthesizing the nitrogen-containing fused ring polymers. Examples of the borate residue include groups represented by the following formulas.

[Chemical Formula 12]

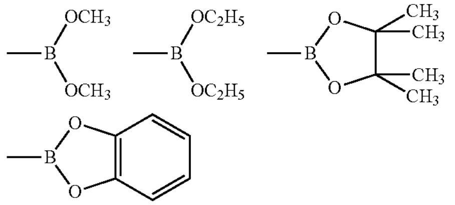

The monovalent group in $R^1$ and $R^2$ may be a group protected by a protecting group. Such a group is preferably a group that is converted to a group illustrated above as a monovalent group by deprotection.

The protecting group refers to a group inert to at least one reaction. Examples of the group protected by a protecting group include groups prepared by replacing an active hydrogen in a group having the active hydrogen with a protecting group such as a trimethylsilyl group (TMS), a triethylsilyl group (TES), a tert-butyldimethylsilyl group (TBS or TBDMS), a triisopropylsilyl group (TIPS) or a tert-butyldiphenylsilyl group (TBDPS). Examples of the group having an active hydrogen include a hydroxy group, an amino group, an alkylamino group, an alkanoylamino group and a sulfo group.

If $R^1$ and/or $R^2$ are a polymerizable group(s) when the nitrogen-containing fused ring compound is contained in an organic thin film, device characteristics and durability of a device may be decreased when the organic thin film is used for fabricating the device. Thus, the polymerizable group(s) may be replaced with an inert group(s).

Examples of the nitrogen-containing fused ring compounds of the present embodiment include nitrogen-containing aromatic ring compounds having a structural unit represented by the formula (2-1), (2-2), (2-3), (2-4), (2-5), (2-6), (2-7) or (2-8).

[Chemical Formula 13]

(2-1)

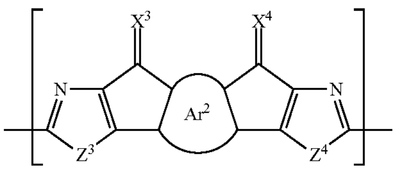

(2-2)

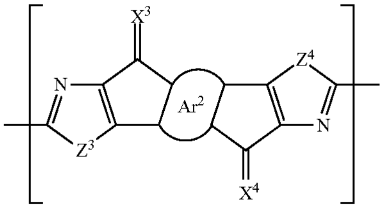

[Chemical Formula 14]

(2-3)

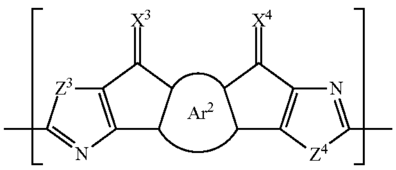

(2-4)

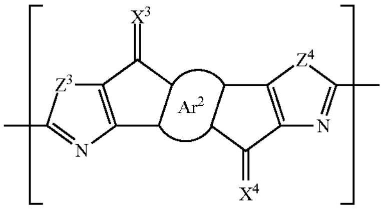

[Chemical Formula 15]

(2-5)

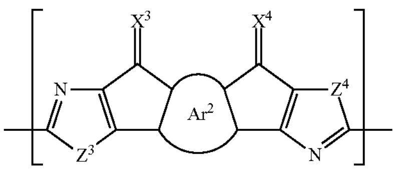

(2-6)

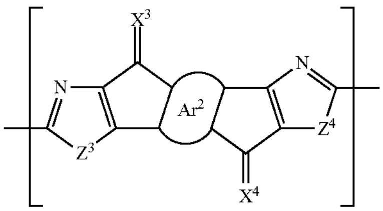

-continued

[Chemical Formula 16]

(2-7)

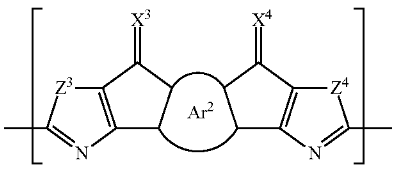

(2-8)

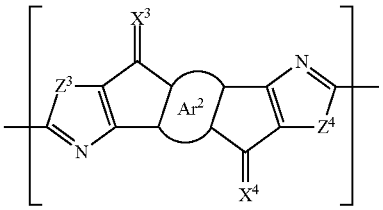

$Ar^2$ represents an aromatic ring having 4 or more carbon atoms which may have a substituent. $X^3$ and $X^4$ each independently represent an oxygen atom, a sulfur atom or a group represented by $=C(A^2)_2$ (wherein $A^2$ represents a hydrogen atom, a halogen atom or a monovalent group, and two $A^2$s may be identical to or different from each other, provided that at least one of the two $A^2$s represents a cyano group, a nitro group, an acyl group, an alkoxycarbonyl group, a carboxyl group, a hydroxy group or a halogen atom), and $Z^3$ and $Z^4$ each independently represent an oxygen atom, a sulfur atom, a selenium atom, a tellurium atom, a group represented by the formula (b-1), a group represented by the formula (b-2), a group represented by the formula (b-3), a group represented by the formula (b-4) or a group represented by the formula (b-5).

[Chemical Formula 17]

(b-1)

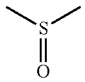

(b-2)

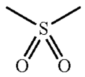

(b-3)

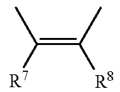

(b-4)

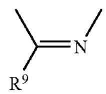

(b-5)

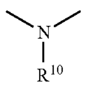

$R^7$, $R^8$, $R^9$ and $R^{10}$ each independently represent a hydrogen atom, a halogen atom or a monovalent group, and $R^7$ and $R^8$ may be bonded to each other to form a ring.

The same aromatic rings as in the above $Ar^1$ can be provided as examples of the aromatic ring in the above $Ar^2$. The same groups as in the above $X^1$ and $X^2$ can be provided as examples of the above $X^3$ and $X^4$. The same groups as in the above $Z^1$ and $Z^2$ can be provided as examples of the above $Z^3$ and $Z^4$.

The same groups as in the above $R^3$ and $R^4$ can be provided as examples of $R^7$ and $R^8$ in the formula (b-3). The same groups as in the above $R^5$ can be provided as examples of $R^9$ in the formula (b-4). The same groups as in the above $R^6$ can be provided as examples of $R^{10}$ in the formula (b-5).

Among the above structural units, structural units represented by the formula (2-1), (2-2), (2-3), (2-4), (2-5) or (2-6) are preferred, and structural units represented by the formula (2-1) or (2-2) are more preferred.

The nitrogen-containing fused ring compounds having such a structural unit have even higher π-conjugation planarity between the rings and can have an even lower LUMO. For this reason, the compounds can be used as organic n-type semiconductors having even higher electron transport properties. Such nitrogen-containing fused ring compounds are chemically more stable and even highly soluble in organic solvents. Therefore, organic thin film devices having higher performance can be manufactured by forming thin films using them.

Such nitrogen-containing fused ring compounds have higher environmental stability. Thus, organic thin film devices having more stable performance even in a normal atmosphere can be manufactured by forming thin films using them.

Examples of the nitrogen-containing fused ring compound having the structural unit represented by the formula (2-1) or the structural unit represented by the formula (2-2) include compounds represented by the formula (7-1) or (7-2).

[Chemical Formula 18]

(7-1)

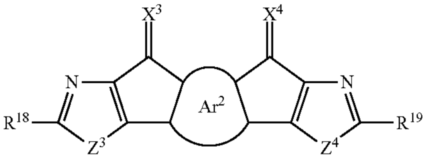

-continued (7-2)

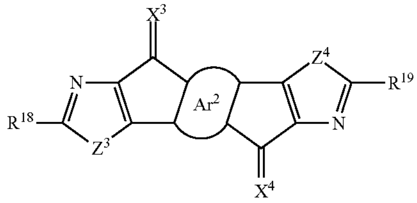

$Ar^2$, $X^3$, $X^4$, $Z^3$ and $Z^4$ are as defined above, and $R^{18}$ and $R^{19}$ each independently represent a hydrogen atom, a halogen atom or a monovalent group. The same groups as in the above $R^1$ and $R^2$ can be provided as examples of $R^{18}$ and $R^{19}$.

The nitrogen-containing fused ring compounds of the present embodiment are more preferably nitrogen-containing fused ring compounds having at least one structural unit selected from the group consisting of a structural unit represented by the formula (3-1) and a structural unit represented by the formula (3-2). Such nitrogen-containing fused ring compounds can exhibit the aforementioned effects of the present invention in a better way.

[Chemical Formula 19]

(3-1)

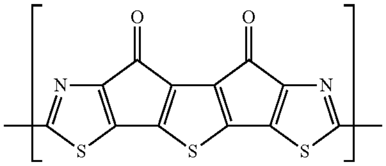

(3-2)

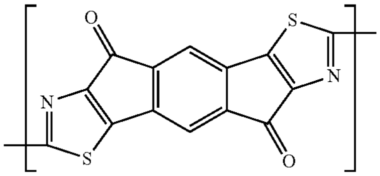

Examples of the nitrogen-containing fused ring compounds of the present embodiment include compounds represented by the formulas (8-1), (8-2), (8-3), (8-4), (8-5), (8-6), (8-7), (8-8), (8-9), (8-10), (8-11), (8-12), (8-13), (8-14), (8-15), (8-16), (8-17), (8-18), (8-19), (8-20), (8-21) and (8-22).

[Chemical Formula 20]

(8-1)

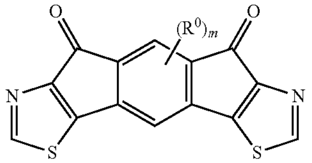

[Chemical Formula 21]

(8-2)

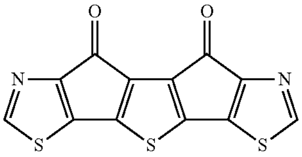

[Chemical Formula 22]

(8-3)

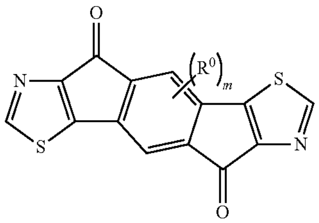

[Chemical Formula 23]

(8-4)

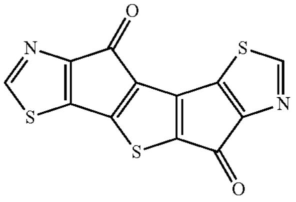

-continued
[Chemical Formula 24]
(8-5)
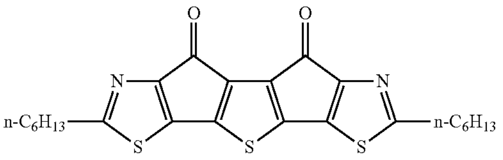
[Chemical Formula 25]
(8-6)
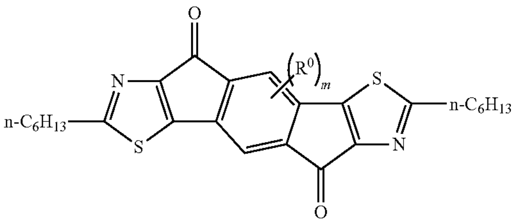
[Chemical Formula 26]
(8-7)
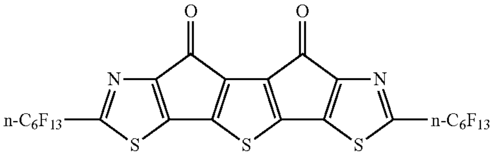
[Chemical Formula 27]
(8-8)
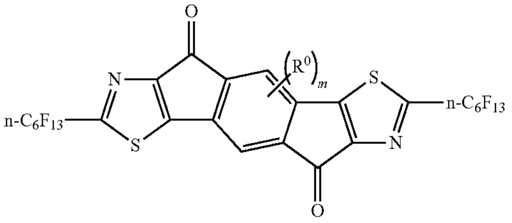
[Chemical Formula 28]
(8-9)
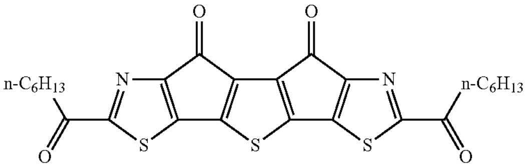
[Chemical Formula 29]
(8-10)
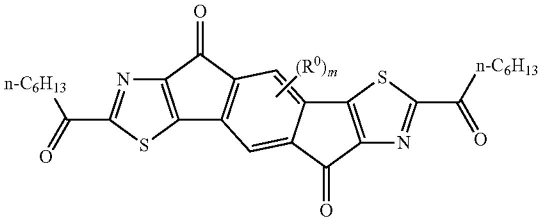
[Chemical Formula 30]
(8-11)
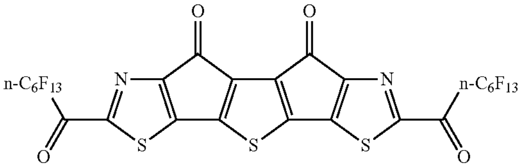
[Chemical Formula 31]
(8-12)
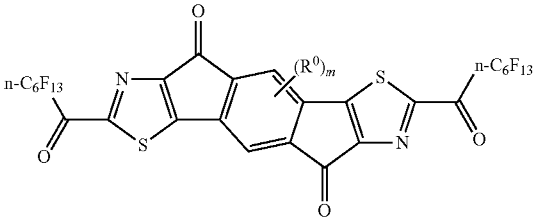
[Chemical Formula 32]
(8-13)
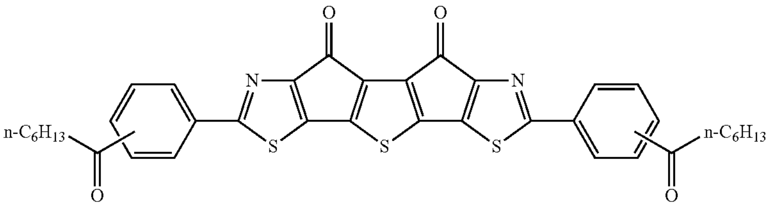
[Chemical Formula 33]
(8-14)
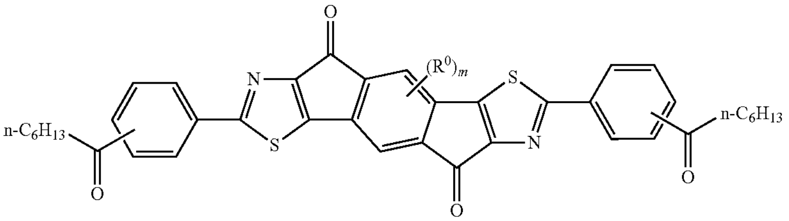

-continued
[Chemical Formula 34]
(8-15)
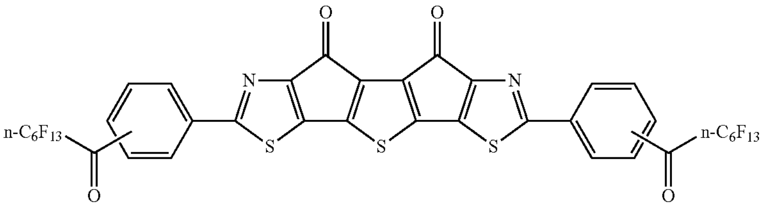
[Chemical Formula 35]
(8-16)
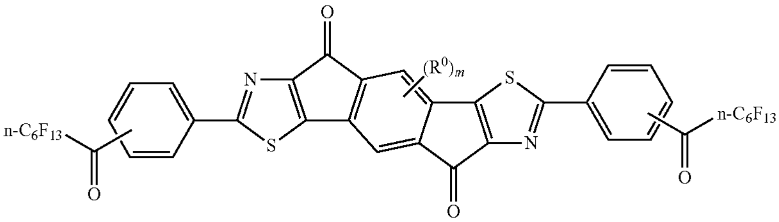
[Chemical Formula 36]
(8-17)
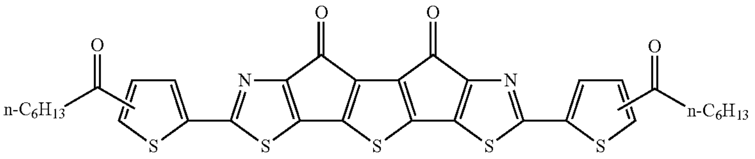
[Chemical Formula 37]
(8-18)
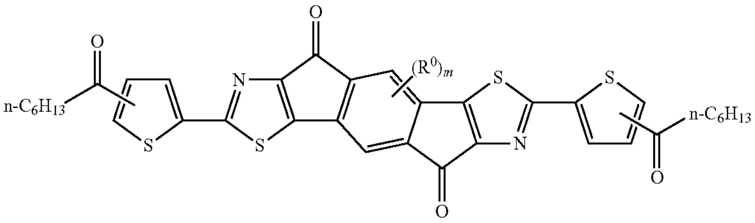
[Chemical Formula 38]
(8-19)
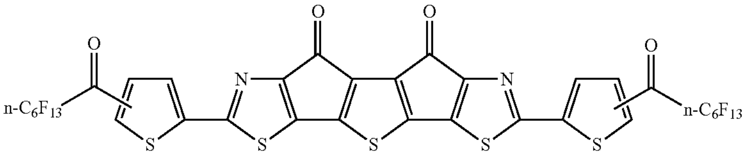
[Chemical Formula 39]
(8-20)
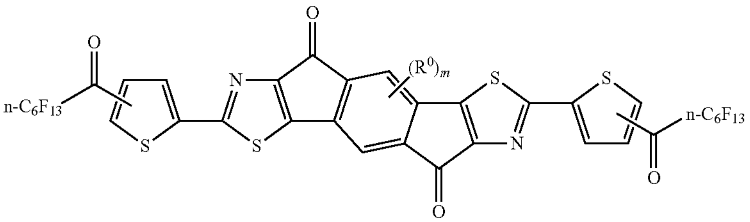

-continued

[Chemical Formula 40]

(8-21)

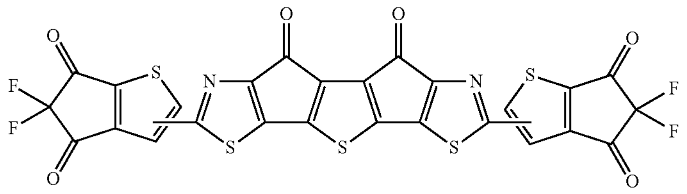

[Chemical Formula 41]

(8-22)

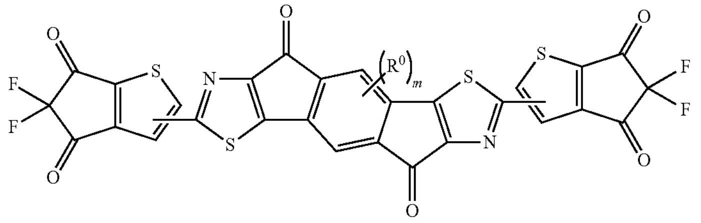

In the formulas, m represents an integer of 0 to 2, and $R^0$ represents a substituent. The substituent is preferably a substituent formed by 20 or less atoms, more preferably a substituent formed by 17 or less atoms. Examples of the substituent include alkyl groups such as a methyl group, an ethyl group, an n-propyl group, an isopropyl group and a sec-propyl group (preferably an alkyl group having 1 to 12 carbon atoms, more preferably an alkyl group having 1 to 10 carbon atoms); alkoxy groups such as a methoxy group, an ethoxy group, an n-propyloxy group, an isopropyloxy group and a sec-propyloxy group (preferably an alkoxy group having 1 to 12 carbon atoms, more preferably an alkoxy group having 1 to 10 carbon atoms); aryl groups such as a phenyl group and a naphthyl group; halogen atoms such as a fluorine atom, a chlorine atom and a bromine atom; a nitro group; and a cyano group. Among these, $R^0$ is preferably an alkyl group, an alkoxy group or an aryl group, more preferably an alkyl group. When m is 2, a plurality of $R^0$s present may be identical to or different from each other.

Next, the nitrogen-containing fused ring polymers of the present embodiment will be described.

The nitrogen-containing fused ring polymers of the present embodiment have a plurality of structural units selected from the group consisting of structural units represented by the formula (1-1) (hereinafter optionally called "first structural units") and structural units represented by the formula (1-2) (hereinafter optionally called "second structural units"). When the nitrogen-containing fused ring polymers have a plurality of the first structural units, the plurality of the first structural units may be identical to or different from each other. When the nitrogen-containing fused ring polymers have a plurality of the second structural units, the plurality of the second structural units may be identical to or different from each other. The same structural units as those represented by the formulas (1-1) and (1-2) in the aforementioned nitrogen-containing fused ring compounds can be provided as examples of the structural units represented by the formulas (1-1) and (1-2) in the nitrogen-containing fused ring polymers.

The nitrogen-containing fused ring polymers of the present embodiment have a plurality of at least one of the first structural units and the second structural units, or have a combination of the first and second structural units. Here, the "structural unit" in the nitrogen-containing fused ring polymer refers to a structural unit forming at least part of the main chain of the nitrogen-containing fused ring polymer. The "polymer" refers to a compound having at least two such "structural units", and also includes both those usually classified as oligomers and those usually classified as polymers.

The total content of the first and second structural units in the nitrogen-containing fused ring polymer is preferably 20 mass % or more, more preferably 50 to 95 mass %, based on the total amount of the nitrogen-containing fused ring polymer.

The first structural unit is preferably a structural unit represented by the formula (2-1). The second structural unit is preferably a structural unit represented by the formula (2-2).

Preferably, the nitrogen-containing fused ring polymers of the present embodiment further have a structural unit represented by the formula (4) (hereinafter optionally called "third structural unit") in addition to the first and second structural units. Solubility or mechanical, thermal or electronic characteristics can be more widely changed by providing the third structural unit. When the nitrogen-containing fused ring polymers have a plurality of the third structural units, the plurality of the third structural units may each be identical or different.

$Ar^3$ represents an arylene group which may have a substituent, or a divalent heterocyclic group which may have a substituent.

The arylene group herein refers to a remaining atomic group obtained by removing two hydrogen atoms from benzene or a fused ring compound prepared by fusing two or more rings. Examples of the fused ring compound include naphthalene, anthracene, tetracene, pentacene, pyrene, perylene and fluorene.

The arylene group is preferably a group having 6 to 60 carbon atoms forming the ring, more preferably a group having 6 to 20 carbon atoms forming the ring. Also, the arylene group is preferably a remaining atomic group obtained by removing two hydrogen atoms from benzene, pentacene, pyrene or fluorene.

The arylene group may have a substituent. Examples of the substituent include a halogen atom, an alkyl group (where the alkyl group has preferably 1 to 12, more preferably 1 to 10, carbon atoms), an unsaturated hydrocarbon group (where the unsaturated hydrocarbon group has preferably 1 to 12, more preferably 1 to 10, carbon atoms), an aryl group, an alkoxy group (where the alkoxy group has preferably 1 to 12, more preferably 1 to 10, carbon atoms), an aryloxy group, a monovalent heterocyclic group, an amino group, a nitro group and a cyano group.

The divalent heterocyclic group herein refers to a remaining atomic group obtained by removing two hydrogen atoms from a heterocyclic compound. Here, the heterocyclic compound refers to an organic compound having a cyclic structure, which has a heteroatom such as an oxygen atom, a sulfur atom, a nitrogen atom, a phosphorus atom, a boron atom or a silicon atom as an atom forming the ring. Examples of the heterocyclic compound include thiophene; compounds prepared by fusing 2 to 6 thiophene rings such as thienothiophene and dithienothiophene; benzothiophene; benzodithiophene; dibenzothiophene; thiazole; pyrrole; pyridine; and pyrimidine.

The divalent heterocyclic group is preferably a group having 3 to 60 carbon atoms forming the ring, more preferably a group having 3 to 20 carbon atoms forming the ring. Also, the divalent heterocyclic group is preferably a remaining atomic group obtained by removing two hydrogen atoms from thiophene, a compound prepared by fusing 2 to 6 thiophene rings such as thienothiophene, benzothiophene, benzodithiophene, dibenzothiophene or thiazole.

The divalent heterocyclic group may have a substituent. Examples of the substituent include a halogen atom, an alkyl group (where the alkyl group has preferably 1 to 12, more preferably 1 to 10, carbon atoms), an unsaturated hydrocarbon group (where the unsaturated hydrocarbon group has preferably 1 to 12, more preferably 1 to 10, carbon atoms), an aryl group, an alkoxy group (where the alkoxy group has preferably 1 to 12, more preferably 1 to 10, carbon atoms), an aryloxy group, a monovalent heterocyclic group, an amino group, a nitro group and a cyano group.

The nitrogen-containing fused ring polymers of the present embodiment preferably have a structure in which any one of the first structural unit and the second structural unit and the third structural unit are adjacent to each other. Providing such a structure can reduce the dihedral angle between the adjacent aromatic rings or heterocycles, improves intramolecular planarity, widens intramolecular 7-conjugation and lowers the LUMO level, thus improving electron transport properties. Here, the dihedral angle is defined as an angle of 0° or more and 90° or less, which is formed by a plane including the heterocycle in the first structural unit or the second structural unit and a plane including a group represented by $Ar^2$ in the third structural unit. When any one of the first structural unit and the second structural unit and the third structural unit are adjacent to each other, the dihedral angle is usually 0 to 45°, typically 0 to 40°, more typically 0 to 30°.

The third structural unit (specifically, $Ar^3$ in the formula (4)) is preferably a structural unit represented by the formula (5).

In the formula, $R^{11}$ and $R^{12}$ each independently represent a hydrogen atom, a halogen atom or a monovalent group, and $R^{11}$ and $R^{12}$ may be bonded to each other to form a ring. The same monovalent groups as in the above $R^3$ or the like can be provided as examples of the monovalent group.

Preferred examples of the monovalent group in $R^{11}$ and $R^{12}$ include alkyl groups such as a methyl group, an ethyl group, an n-propyl group, an isopropyl group and a sec-propyl group (preferably an alkyl group having 1 to 12 carbon atoms, more preferably an alkyl group having 1 to 10 carbon atoms); alkoxy groups such as a methoxy group, an ethoxy group, an n-propyloxy group, an isopropyloxy group and a sec-propyloxy group (preferably an alkoxy group having 1 to 12 carbon atoms, more preferably an alkoxy group having 1 to 10 carbon atoms); aryl groups such as a phenyl group and a naphthyl group; halogen atoms such as a fluorine atom, a chlorine atom and a bromine atom; a nitro group; and a cyano group. Among these, the monovalent group in $R^{11}$ and $R^{12}$ is more preferably an alkyl group, an alkoxy group or an aryl group, still more preferably an alkyl group.

$Z^5$ represents an oxygen atom, a sulfur atom, a selenium atom, a tellurium atom, a group represented by the formula (c-1), a group represented by the formula (c-2), a group represented by the formula (c-3), a group represented by the formula (c-4) or a group represented by the formula (c-5).

$R^{13}$, $R^{14}$, $R^{15}$ and $R^{16}$ each independently represent a hydrogen atom, a halogen atom or a monovalent group, and $R^{13}$ and $R^{14}$ may be bonded to each other to form a ring.

The same groups as in the above $R^3$ and $R^4$ can be provided as examples of $R^{13}$ and $R^{14}$ in the formula (c-3). The same groups as in the above $R^5$ can be provided as examples of $R^{15}$ in the formula (c-4). The same groups as in the above $R^6$ can be provided as examples of $R^{16}$ in the formula (c-5).

$Z^5$ is preferably an oxygen atom, a sulfur atom, a selenium atom, a group represented by the formula (c-3), a group represented by the formula (c-4) or a group represented by the formula (c-5), more preferably a sulfur atom, a selenium atom, a group represented by the formula (c-3) or a group represented by the formula (c-5), still more preferably a sulfur atom, because this provides characteristic electrical properties (such as highest occupied molecular orbital (HOMO) or LUMO level more suitable for electron transport) and various electrical characteristics (such as even higher electron transport properties).

The ratio between the total content of the first and second structural units $C_{1+2}$ (moles) and the content of the third structural unit $C_3$ (moles) in the nitrogen-containing fused ring polymer, $C_3/C_{1+2}$, is preferably 0.05 to 3, more preferably 0.2 to 2, still more preferably 0.5 to 1.

The nitrogen-containing fused ring polymers of the present embodiment are preferably polymers represented by the formula (9-1), (9-2), (9-3) or (9-4), because this further increase electron transport properties.

[Chemical Formula 42]

(9-1)

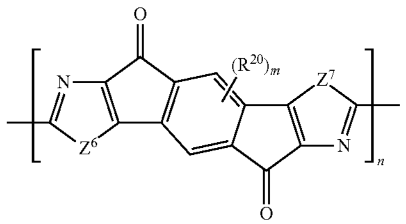

[Chemical Formula 43]

(9-2)

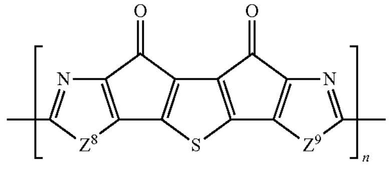

-continued

[Chemical Formula 44]

(9-3)

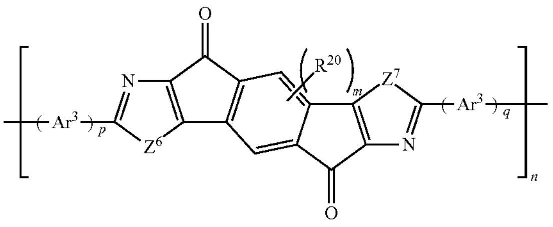

[Chemical Formula 45]

(9-4)

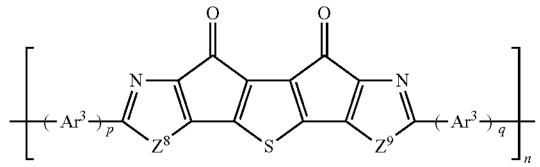

$Z^6$ and $Z^7$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5), $Z^8$ and $Z^9$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5), m represents an integer of 0 to 2, p and q each independently represent an integer of 0 to 6, n represents an integer of 2 to 500, and $R^{20}$ represents a substituent.

The same groups as in the above $Z^1$ and $Z^2$ can be provided as examples of $Z^6$ and $Z^7$. The same groups as in the above $Z^1$ and $Z^2$ can be provided as examples of $Z^8$ and $Z^9$. The same groups as in the above $R^0$ can be provided as examples of $R^{20}$.

p+q is preferably 0 to 6, more preferably 0 to 3. n is preferably an integer of 2 to 100, more preferably an integer of 2 to 20.

In the nitrogen-containing fused ring polymers represented by the formula (9-1), (9-2), (9-3) or (9-4), all of $Z^6$, $Z^7$, $Z^8$ and $Z^9$ are preferably sulfur atoms. $Ar^3$ is preferably a structural unit represented by the formula (5).

The nitrogen-containing fused ring polymers of the present embodiment may have a group illustrated as $R^1$ and $R^2$ in the above formulas (6-1) and (6-2) at the terminal, for example.

Examples of the group at the terminal of the nitrogen-containing fused ring polymer (hereinafter called "terminal group") include a hydrogen atom, a fluorine atom, an alkyl group (where the alkyl group has preferably 1 to 12, more preferably 1 to 10, carbon atoms), an alkoxy group (where the alkoxy group has preferably 1 to 12, more preferably 1 to 10, carbon atoms), an acyl group, a carbamoyl group, an aryl group, a monovalent heterocyclic group, a group having an a-fluorocarbonyl structure, an electron-donating group and an electron-accepting group. Hydrogen atoms in these groups may be replaced with fluorine atoms.

Among these, groups in which all hydrogen atoms are replaced with fluorine atoms, for example, a perfluoroalkyl group, a perfluoroalkoxy group and a perfluorophenyl group are preferred. Groups having a conjugated bond continuous with the conjugated structure of the main chain are also preferred. Such groups include an aryl group and a monovalent heterocyclic group which are linked to the conjugated structure of the main chain through a carbon-carbon bond.

The terminal group may be a polymerizable group. Such nitrogen-containing fused ring polymers can be used as raw material compounds for synthesizing nitrogen-containing fused ring polymers having an even higher molecular weight. The terminal groups at both terminals of the nitrogen-containing fused ring polymers are preferably polymerizable groups when the polymers are used as such raw material compounds. Here, polymerizable groups include the same groups as described above.

If the terminal group is a polymerizable group when the nitrogen-containing fused ring polymer is contained in an organic thin film, device characteristics and durability of a device may be decreased when the organic thin film is used for fabricating the device. Therefore, the polymerizable group may be replaced with an inert group.

The nitrogen-containing fused ring polymers of the present embodiment are particularly preferably polymers represented by the formulas (10-1), (10-2), (10-3), (10-4), (10-5), (10-6), (10-7), (10-8), (10-9) and (10-10).

[Chemical Formula 46]

(10-1)

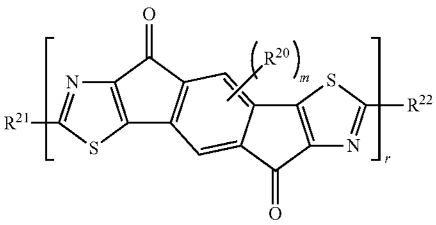

[Chemical Formula 47]

(10-2)

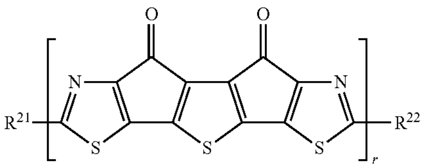

[Chemical Formula 48]

(10-3)

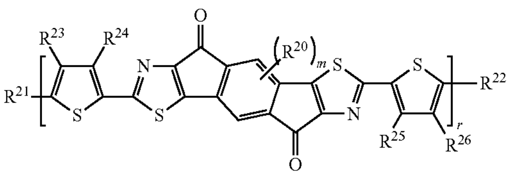

[Chemical Formula 49]

(10-4)

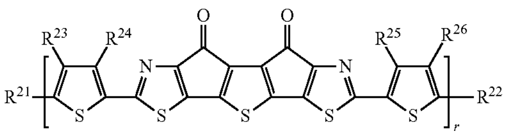

-continued

[Chemical Formula 50]

(10-5)

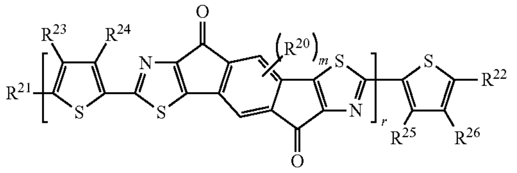

[Chemical Formula 51]

(10-6)

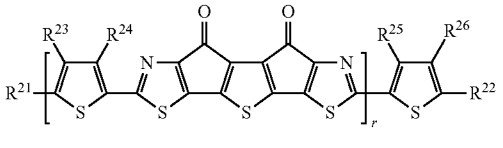

[Chemical Formula 52]

(10-7)

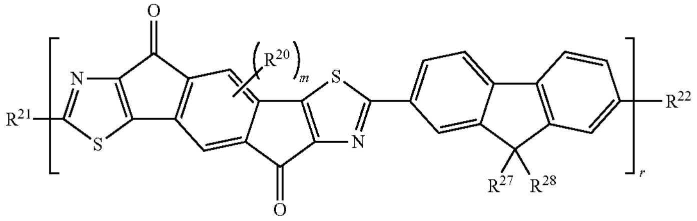

[Chemical Formula 53]

(10-8)

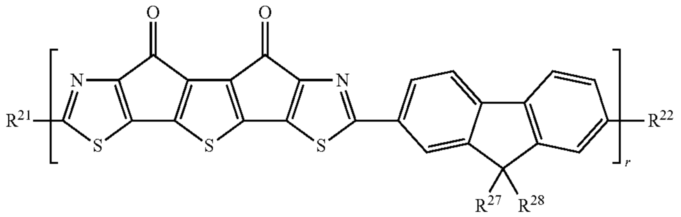

[Chemical Formula 54]

(10-9)

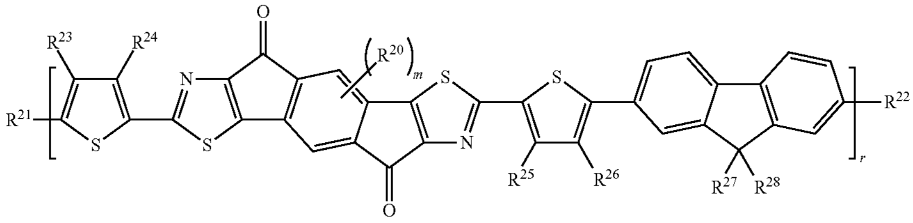

[Chemical Formula 55]

(10-10)

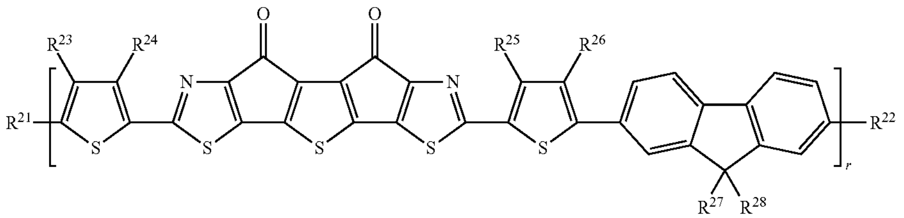

m and $R^{20}$ are as defined above, r represents an integer of 2 or more, $R^{21}$ and $R^{22}$ each independently represent a hydrogen atom, a halogen atom or a monovalent group, $R^{23}$, $R^{24}$, $R^{25}$ and $R^{26}$ each independently represent a hydrogen atom, a halogen atom or a monovalent group, $R^{23}$ and $R^{24}$ may be bonded to each other to form a ring, and $R^{25}$ and $R^{26}$ may be bonded to each other to form a ring, and $R^{27}$ and $R^{28}$ each independently represent a hydrogen atom, a halogen atom or a monovalent group.

The same monovalent groups as in the above $R^1$ and $R^2$ can be provided as examples of the monovalent group in the above $R^{21}$ and $R^{22}$. The same monovalent groups as in the above $R^3$, $R^4$, $R^5$ and $R^6$ can be provided as examples of the monovalent group in $R^{23}$, $R^{24}$, $R^{25}$ and $R^{26}$. The same monovalent groups as in the above $R^3$, $R^4$, $R^5$ and $R^6$ can be provided as examples of the monovalent group in $R^{27}$ and $R^{28}$.

Preferred examples of the monovalent group in $R^{27}$ and $R^{28}$ include preferably alkyl groups such as a methyl group, an ethyl group, an n-propyl group, an isopropyl group and a sec-propyl group (preferably an alkyl group having 1 to 12 carbon atoms, more preferably an alkyl group having 1 to 10 carbon atoms); alkoxy groups such as a methoxy group, an ethoxy group, an n-propyloxy group, an isopropyloxy group and a sec-propyloxy group (preferably an alkoxy group having 1 to 12 carbon atoms, more preferably an alkoxy group having 1 to 10 carbon atoms); aryl groups such as a phenyl group and a naphthyl group; halogen atoms such as a fluorine atom, a chlorine atom and a bromine atom; a nitro group; and a cyano group, for example. Among these, an alkyl group, an alkoxy group or an aryl group is preferred, and an alkyl group is more preferred.

The monovalent group in $R^{21}$ and $R^{22}$ is preferably a fluoroalkyl group or a group having an α-fluorocarbonyl structure, more preferably a perfluoroalkyl group or a group having an α-fluorocarbonyl structure.

When a plurality of $R^{20}$s, $R^{23}$s, $R^{24}$s, $R^{25}$s, $R^{26}$s, $R^{27}$s or $R^{28}$s are present in the nitrogen-containing fused ring polymer, they may be identical to or different from each other. When a plurality of $R^{20}$s, $R^{23}$s, $R^{24}$s, $R^{25}$s, $R^{26}$s, $R^{27}$s or $R^{28}$s are present, they are preferably identical to each other, taking easy synthesis of the nitrogen-containing fused ring polymer into consideration.

When the nitrogen-containing fused ring polymer is used for the manufacture of an organic thin film, r can be selected according to the method for manufacturing the organic thin film. For example, if the nitrogen-containing fused ring polymer is sublimable, an organic thin film containing the nitrogen-containing fused ring polymer can be manufactured using chemical vapor deposition such as vacuum deposition. In this case, r is preferably an integer of 2 to 10, more preferably an integer of 2 to 5.

On the other hand, when using a method of manufacturing an organic thin film by applying a solution in which the nitrogen-containing fused ring polymer is dissolved in an organic solvent, r is preferably an integer of 3 to 500, more preferably an integer of 6 to 300, still more preferably an integer of 20 to 200. The polystyrene-reduced number average molecular weight of the nitrogen-containing fused ring polymer is preferably $1\times10^3$ to $1\times10^7$, more preferably $1\times10^4$ to $1\times10^6$, because this provides high uniformity of the film formed by application.

The nitrogen-containing fused ring polymers of the present embodiment are also particularly preferably polymers represented by the formulas (11-1), (11-2), (11-3), (11-4), (11-5) and (11-6).

[Chemical Formula 56]

(11-1)

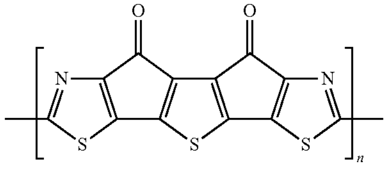

[Chemical Formula 57]

(11-2)

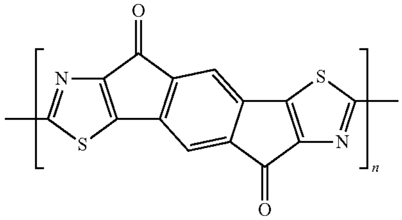

-continued

[Chemical Formula 58]

(11-3)

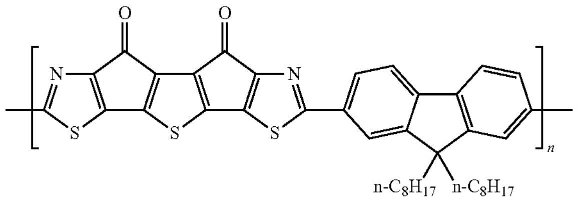

[Chemical Formula 59]

(11-4)

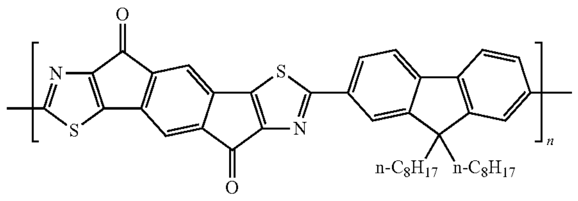

[Chemical Formula 60]

(11-5)

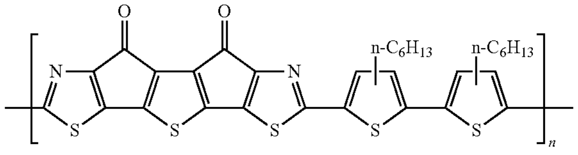

[Chemical Formula 61]

(11-6)

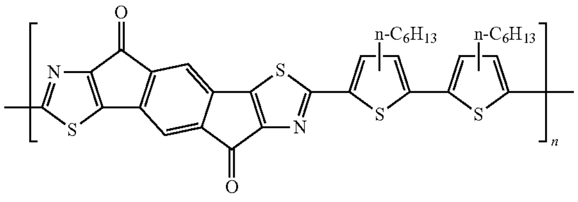

In the formulas, n represents an integer of 2 to 500 and is preferably an integer of 2 to 100, more preferably an integer of 2 to 20.

Next, the methods for manufacturing the nitrogen-containing fused ring compounds and the nitrogen-containing fused ring polymers of the present embodiment will be described. The nitrogen-containing fused ring compounds and the nitrogen-containing fused ring polymers of the present embodiment may be manufactured by any methods, but are preferably manufactured by the manufacturing methods described below.

First, the methods for manufacturing the nitrogen-containing fused ring compounds of the present embodiment will be described using methods for manufacturing nitrogen-containing fused ring compounds having a structural unit represented by the formula (2-1) by way of example.

The nitrogen-containing fused ring compounds of the present embodiment can be manufactured according to the following scheme 1, for example.

Scheme 1

[Chemical Formula 62]

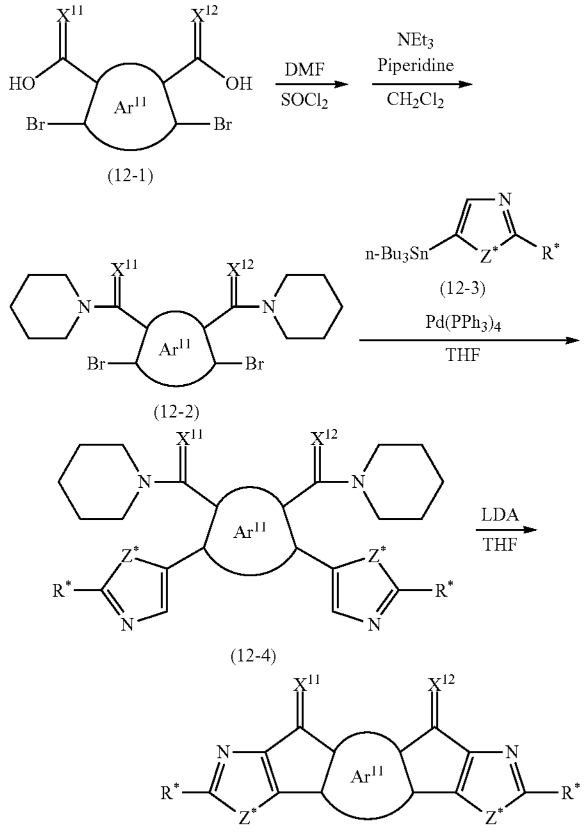

(12-5)

In the scheme 1, $Ar^{11}$ represents an aromatic ring having 4 or more carbon atoms which may have a substituent, $X^{11}$ and $X^{12}$ each independently represent an oxygen atom, a sulfur atom or a group represented by $=C(A^1)_2$, R* represents a hydrogen atom, a halogen atom or a monovalent group, and Z* represents an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5).

The same groups as in the above $Ar^1$ can be provided as examples of $Ar^{11}$. The same groups as in the above $X^1$ and $X^2$ can be provided as examples of $X^{11}$ and $X^{12}$. The same groups as in the above $R^1$ and $R^2$ can be provided as examples of R*. The same groups as in the above $Z^1$ and $Z^2$ can be provided as examples of Z*.

Specifically, in the first step, a compound represented by the formula (12-1) (hereinafter optionally called "compound (12-1)"; hereinafter, the same applies to a compound represented by the formula (12-2) or the like) is reacted with thionyl chloride ($SOCl_2$) in the presence of a catalytic amount of dimethylformamide (hereinafter called "DMF") and then reacted with triethylamine and piperidine in methylene chloride further to provide a compound (12-2). The compound (12-1) can be reacted with thionyl chloride by mixing a catalytic amount of DMF, the compound (12-1), and 200 to 4000 mol % of thionyl chloride based on the total amount of the compound (12-1), and heating and refluxing the mixture, for example.

Next, in the second step, the compound (12-2) is reacted with a compound (12-3) in the presence of a palladium catalyst to provide a compound (12-4). This reaction can be performed by heating and refluxing the compound (12-2), the compound (12-3), and 0.5 to 20 mol % of the palladium catalyst based on the total amount of the compound (12-2) in tetrahydrofuran (hereinafter called "THF"), for example. Tetrakis(triphenylphosphine)palladium ($Pd(PPh_3)$) or the like can be used as the palladium catalyst.

Next, in the third step, a compound (12-5) can be provided by cyclization reaction of the compound (12-4) in the presence of lithium diisopropylamide (LDA). This reaction can be performed using 200 to 3000 mol % of lithium diisopropylamide based on the total amount of the compound (12-4) in THF at a temperature of −78 to 0° C., for example.

In the first step, an acid chloride such as oxalyl chloride may also be used in place of thionyl chloride. In the second step, toluene or chlorobenzene may also be used in place of THF. In the third step, lithium hexamethyldisilazide may also be used in place of lithium diisopropylamide.

According to the manufacturing method shown in the following scheme 2, nitrogen-containing fused ring compounds where various R** groups are introduced (i.e., compounds represented by the formula (12-10)) can be manufactured using nitrogen-containing fused ring compounds of the formula (12-5) where R* is a hydrogen atom (i.e., compounds represented by the formula (12-6)).

The scheme 2 shows a manufacturing example using a nitrogen-containing fused ring compound of the formula (12-5) where $X^{11}$ and $X^{12}$ are oxygen atoms. Even when $X^{11}$ and $X^{12}$ are other than oxygen atoms, nitrogen-containing fused ring compounds where various R** groups are introduced can be manufactured in the same manner as in the scheme 2 except for carrying out a step of protecting groups represented by $=X^{11}$ and $=X^{12}$ instead of a step of providing a compound represented by the formula (12-7).

Scheme 2

[Chemical Formula 63]

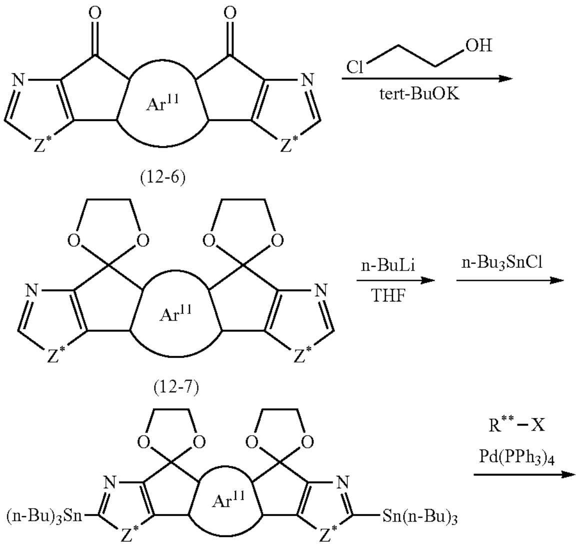

(12-8)

-continued

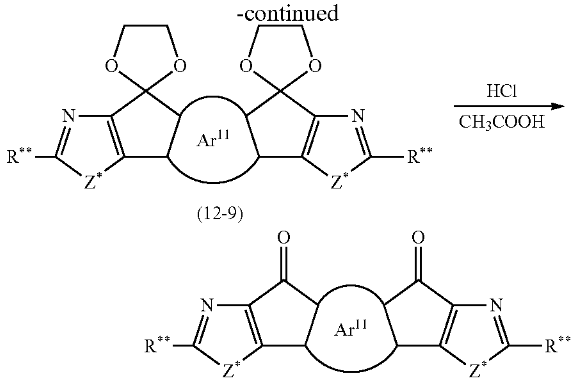

(12-9)

(12-10)

In the scheme 2, $Ar^{11}$ and Z* are as defined above, R represents a hydrogen atom, a halogen atom or a monovalent group, and X represents a halogen atom. The same groups as in the above $R^1$ and $R^2$ can be provided as examples of R.

Specifically, in the first step, the carboxyl group in a compound (12-6) is protected first. More specifically, a compound (12-7) can be provided by reacting the compound (12-6) with 2-chloroethanol in the presence of tert-butoxypotassium (tert-BuOK), for example. The carboxyl group may also be protected by acetalizing the compound by reacting with 2,2-dibutyl-1,3-propenediol or the like in place of 2-chloro ethanol.

Next, in the second step, the compound (12-7) is reacted with n-butyllithium (n-BuLi) in THF and then reacted with tributyltin chloride (n-$Bu_3SnCl$) to provide a compound (12-8).

Further, in the third step, the compound (12-8) is reacted with a compound represented by $R^{}$—X in the presence of a palladium catalyst to provide a compound (12-9). This reaction can be performed by heating and refluxing the compound (12-8), the compound represented by $R^{}$—X, and 0.5 to 20 mol % of the palladium catalyst based on the total amount of the compound (12-8) in toluene. Tetrakis(triphenylphosphine)palladium ($Pd(PPh_3)$) or the like can be used as the palladium catalyst.

Next, in the fourth step, a compound (12-10) can be provided by reacting the compound (12-9) with hydrochloric acid in acetic acid.

In the first step, a ketal reaction under general acidic conditions or a reaction with ethylene glycol in the presence of p-toluenesulfonic acid may also be used in place of the reaction using 2-chloroethanol as the reaction of protecting the carboxyl group. In the second step, trimethyltin chloride may also be used in place of tributyltin chloride. In the third step, THF or chlorobenzene may also be used in place of toluene. In the fourth step, sulfuric acid or a chloroform-acetic acid mixed solvent may also be used in place of acetic acid.

In the foregoing, although the nitrogen-containing fused ring compounds having a structural unit represented by the formula (2-1) have been described by way of example, nitrogen-containing fused ring compounds having a structural unit represented by the formula (2-2), (2-3), (2-4), (2-5), (2-6), (2-7) or (2-8) can be similarly manufactured by changing the above compound (12-1), compound (12-3) and compound (12-4) as appropriate.

When the nitrogen-containing fused ring compounds of the present embodiment are used as materials for organic thin film devices, their purity may affect device characteristics. Thus, the nitrogen-containing fused ring compounds obtained by the above manufacturing methods are preferably purified by methods such as distillation, sublimation purification, and recrystallization, for example.

Other reaction conditions, reaction reagents and the like than the above examples can also be selected in the above manufacturing methods.

Next, the methods for manufacturing the nitrogen-containing fused ring polymers of the present embodiment will be described using a method for manufacturing a nitrogen-containing fused ring polymer having a structural unit represented by the formula (2-1) as a first structural unit, a structural unit represented by the formula (2-2) as a second structural unit, and a structural unit represented by the formula (4) and a structural unit represented by the formula (5) as third structural units by way of example.

The nitrogen-containing fused ring polymers of the present embodiment can be manufactured by reacting compounds represented by the following formulas (13-1), (13-2), (13-3) and (13-4) (hereinafter optionally called "monomer (13-1)", "monomer (13-2)", "monomer (13-3)" and "monomer (13-4)", respectively) as raw materials, for example.

[Chemical Formula 64]

(13-1)

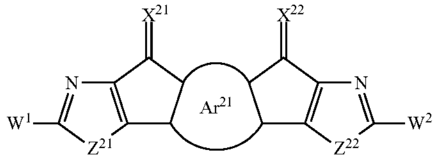

[Chemical Formula 65]

(13-2)

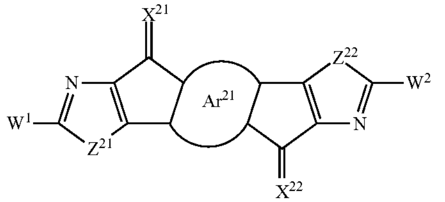

[Chemical Formula 66]

(13-3)

$$W^1—Ar^{13}—W^2$$

[Chemical Formula 67]

(13-4)

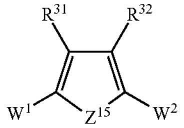

In the formulas, $Ar^{21}$ represents an aromatic ring having 4 or more carbon atoms which may have a substituent, $X^{21}$ and $X^{22}$ each independently represent an oxygen atom, a sulfur atom or a group represented by $=C(A^1)_2$, $Z^{21}$ and $Z^{22}$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5), $Ar^{13}$ represents an arylene group which may have a substituent, or a heterocyclic group which may have a substituent, $R^{31}$ and $R^{32}$ each independently represent a hydrogen atom, a halogen atom or a monovalent group, $Z^{15}$ represents an oxygen atom, a sulfur atom, a selenium atom, a tellurium atom, a group represented by the formula (c-1), a group represented by the formula (c-2), a group represented by the formula (c-3), a group represented by the formula (c-4) or a group represented by the formula (c-5), and $W^1$ and $W^2$ each independently represent a hydrogen atom, a halogen atom or a polymerizable group.

The same groups as in the above $Ar^1$ can be provided as examples of $Ar^{21}$. The same groups as in the above $X^1$ and $X^2$ can be provided as examples of $X^{21}$ and $X^{22}$. The same groups as in the above $Z^1$ and $Z^2$ can be provided as examples of $Z^{21}$ and $Z^{22}$. The same groups as in the above $Ar^3$ can be provided as examples of $Ar^{13}$. The same groups as in the above $R^{11}$ and $R^{12}$ can be provided as examples of $R^{31}$ and $R^{32}$. The same groups as in the above $Z^5$ can be provided as examples of $Z^{15}$. The same polymerizable groups as above can be provided as examples of the polymerizable groups in $W^1$ and $W^2$.

$W^1$ and $W^2$ are each preferably a halogen atom, an alkyl sulfonate group, an aryl sulfonate group, an arylalkyl sulfonate group, an alkylstannyl group, a borate residue or a boric acid residue, because the reaction is easily performed in the synthesis.

Examples of the reaction method used in the manufacture of the nitrogen-containing fused ring polymers of the present embodiment include a method using Wittig reaction, a method using Heck reaction, a method using Horner-Wadsworth-Emmons reaction, a method using Knoevenagel reaction, a method using Suzuki coupling reaction, a method using Grignard reaction, a method using Stille reaction, a method using a Ni(0) catalyst, a method using an oxidizing agent such as $FeCl_3$, a method using electrochemical oxidation reaction, or a method by decomposition of an intermediate compound having an appropriate leaving group.

Among these, a method using Wittig reaction, a method using Heck reaction, a method using Horner-Wadsworth-Emmons reaction, a method using Knoevenagel reaction, a method using Suzuki coupling reaction, a method using Grignard reaction, a method using Stille reaction and a method using a Ni(0) catalyst are preferred because the structure of the compound is easily controlled. A method using Suzuki coupling reaction, a method using Grignard reaction, a method using Stille reaction and a method using a Ni(0) catalyst are preferred because the raw materials are readily available and the reaction is simply operated.

The monomer (13-1), the monomer (13-2), the monomer (13-3) and the monomer (13-4) can be dissolved in organic solvents and reacted using alkalis or appropriate catalysts at the melting points or higher and the boiling points or lower of the organic solvents as necessary.

The organic solvents are preferably sufficiently deoxidized to suppress side reaction, depending on the various monomers and reactions used. The reaction is preferably allowed to proceed in an inert atmosphere. Further, the organic solvents are also preferably dehydrated (except for reactions in two-phase systems with water such as Suzuki coupling reaction).

Alkalis or appropriate catalysts are added as necessary to allow the reaction to proceed. They may be selected depending on the reaction used. Alkalis or catalysts are preferably those that can be sufficiently dissolved in solvents used in the reaction.

When the nitrogen-containing fused ring polymers of the present embodiment are used as materials for organic thin film devices, their purity affects device characteristics. Thus, the monomers before the reaction are preferably reacted (polymerized) after purification by methods such as distillation, sublimation purification and recrystallization. After synthesis of the nitrogen-containing fused ring polymers, they are preferably purified by reprecipitation, separation by chromatography, or the like.

Examples of the organic solvents used in the reaction include saturated hydrocarbons such as pentane, hexane, heptane, octane and cyclohexane; unsaturated hydrocarbons such as benzene, toluene, ethylbenzene and xylene; halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane; halogenated unsaturated hydrocarbons such as chlorobenzene, dichlorobenzene and trichlorobenzene; alcohols such as methanol, ethanol, propanol, isopropanol, butanol and tert-butyl alcohol; carboxylic acids such as formic acid, acetic acid and propionic acid; and ethers such as dimethyl ether, diethyl ether, methyl tert-butyl ether, THF, tetrahydropyran and dioxane. Inorganic acids such as hydrochloric acid, bromic acid, hydrofluoric acid, sulfuric acid and nitric acid may also be used in place of organic solvents. When inorganic acids are used in place of organic solvents, the reaction temperatures can be the melting points or higher and the boiling points or lower of the inorganic acids.

After the reaction, the nitrogen-containing fused ring polymers can be provided by performing common post-treatment such as extraction with an organic solvent and evaporation of the solvent after quenching the reaction with water, for example. The resulting nitrogen-containing fused ring polymers can be isolated and separated by methods such as separation by chromatography and recrystallization.

In the foregoing, although the description has been made using a method for manufacturing a nitrogen-containing fused ring polymer having a structural unit represented by the formula (2-1) as a first structural unit, a structural unit represented by the formula (2-2) as a second structural unit, and a structural unit represented by the formula (4) and a structural unit represented by the formula (5) as third structural units by way of example, nitrogen-containing fused ring polymers having other structural units can also be manufactured in the same manner as in the above reaction by appropriately selecting the monomers.

When the nitrogen-containing fused ring polymers of the present embodiment are used as materials for organic thin film devices, their purity may affect device characteristics. Thus, the nitrogen-containing fused ring polymers obtained by the above manufacturing methods are preferably purified by methods such as distillation, sublimation purification, and recrystallization, for example.

Next, the organic thin films of the present embodiment will be described. The organic thin films of the present embodiment comprise the nitrogen-containing fused ring compounds and/or the nitrogen-containing fused ring polymers of the present embodiment (hereinafter collectively called "nitrogen-containing compounds of the present embodiment").

The organic thin films of the present embodiment has a thickness of usually 1 nm to 100 preferably 2 nm to 1000 nm, more preferably 5 nm to 500 nm, still more preferably 20 nm to 200 nm.

The organic thin films may contain one nitrogen-containing compound of the present embodiment singly, or may contain two or more nitrogen-containing compounds of the present embodiment. In order to improve electron transport properties or hole transport properties of the organic thin films, low-molecular-weight compounds or polymer compounds having electron transport properties (hereinafter called "electron transport materials") or low-molecularweight compounds or polymer compounds having hole transport properties (hereinafter called "hole transport materials") can also be mixed with the nitrogen-containing compounds of the present embodiment and used.

Known materials' can be used as hole transport materials, and examples thereof include pyrazoline derivatives, arylamine derivatives, stilbene derivatives, triaryldiamine derivatives, oligothiophene and derivatives thereof, polyvinylcarbazole and derivatives thereof, polysilane and derivatives thereof, polysiloxane derivatives having aromatic amines in the side chains or main chains, polyaniline and derivatives thereof, polythiophene and derivatives thereof, polypyrrole and derivatives thereof, polyarylenevinylene and derivatives thereof, and polythienylenevinylene and derivatives thereof.

Known materials can be used as electron transport materials, and examples thereof include metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, or 8-hydroxyquinoline and derivatives thereof, polyquinoline and derivatives thereof, polyquinoxaline and derivatives thereof, polyfluorene and derivatives thereof, and fullerenes such as $C_{60}$ fullerene, and derivatives thereof.

The organic thin films of the present embodiment may comprise charge generating materials to generate charges by light absorbed in the organic thin films. Known materials can be used as charge generating materials, and examples thereof include azo compounds and derivatives thereof, diazo compounds and derivatives thereof, non-metallic phthalocyanine, compounds and derivatives thereof, metallic phthalocyanine compounds and derivatives thereof, perylenes compounds and derivatives thereof, polycyclic quinone compounds and derivatives thereof, squarylium compounds and derivatives thereof, azulenium compounds and derivatives thereof, thiapyrylium compounds and derivatives thereof, and fullerenes such as $C_{60}$ fullerene, and derivatives thereof.

The organic thin films of the present embodiment may comprise materials necessary for exhibiting various functions. Examples include sensitizers for sensitizing functions to generate charges by absorbed light, stabilizers for increasing stability, and UV absorbers for absorbing ultraviolet (UV) light.

The organic thin films of the present embodiment may comprise polymer materials other than the nitrogen-containing compounds of the present embodiment as polymer binders in order to increase mechanical characteristics. As polymer binders, those that do not extremely interfere with charge transport properties or hole transport properties are preferred, and those that do not strongly absorb visible light are also preferably used.

Examples of such polymer binders include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride and polysiloxane.

Examples of the methods for manufacturing the organic thin films of the present embodiment include methods of forming films from solutions containing the nitrogen-containing compounds of the present embodiment, and electron transport materials or hole transport materials and polymer binders mixed as necessary. When the nitrogen-containing compounds of the present embodiment are sublimable, thin films can be formed by vacuum deposition.

The organic thin films of the present embodiment can also be manufactured by preparing thin films containing precursors of the nitrogen-containing compounds of the present embodiment (e.g., the above compound (12-9)) and converting the precursors to the nitrogen-containing compounds of the present embodiment by heating or the like. The organic thin films manufactured in this manner may comprise the above precursors and side-products thereof in addition to the nitrogen-containing compounds of the present embodiment, unless the characteristics are greatly affected.

The solvents used for forming films from solutions may be those that can dissolve the nitrogen-containing compounds of the present embodiment, and electron transport materials or hole transport materials and polymer binders mixed.

Examples of the solvents used for forming the organic thin films of the present embodiment from solutions include unsaturated hydrocarbons such as toluene, xylene, mesitylene, tetralin, decalin, bicyclohexyl, n-butylbenzene, sec-butylbenzene and tert-butylbenzene; halogenated saturated hydrocarbons such as carbon tetrachloride, chloroform, dichloromethane, dichloroethane, chlorobutane, bromobutane, chloropentane, bromopentane, chlorohexane, bromohexane, chlorocyclohexane and bromocyclohexane; halogenated unsaturated hydrocarbons such as chlorobenzene, dichlorobenzene and trichlorobenzene; and ethers such as THF and tetrahydropyran. Usually, 0.1 mass % or more of the nitrogen-containing compounds of the present embodiment can be dissolved in such solvents depending on the structures and molecular weights of the nitrogen-containing compounds of the present embodiment.

Application methods such as spin coating, casting, microgravure coating, gravure coating, bar coating, roll coating, wire bar coating, dip coating, spray coating, screen printing, flexographic printing, offset printing, inkjet printing, dispenser printing, nozzle coating and capillary coating can be used as methods of forming films from solutions. Among these, spin coating, flexographic printing, inkjet printing, dispenser printing, nozzle coating and capillary coating are preferred.

The process of manufacturing the organic thin films of the present embodiment may include a step of orienting the nitrogen-containing compounds of the present embodiment. In the organic thin films in which the nitrogen-containing compounds of the present embodiment are oriented by this step, main chain molecules or side chain molecules are arranged in one direction, and thus electron mobility or hole mobility is improved.

Methods known as techniques for orienting liquid crystals can be used as methods for orienting the nitrogen-containing compounds of the present embodiment. In particular, rubbing, photoorientation, shearing (shear stress application) and drawing-up coating are simple, useful and easily utilizable as orientation techniques, with rubbing and shearing being preferred.

The process of manufacturing the organic thin films of the present embodiment may include a step of annealing after forming films. This step improves the quality of the organic thin films, for example, promotes interaction between the nitrogen-containing compounds of the present embodiment, and improves electron mobility or hole mobility. The annealing temperature is preferably a temperature between 50° C. and a temperature near the glass transition temperature (Tg) of the nitrogen-containing compound of the present embodiment, more preferably a temperature between (Tg−30° C.)

and Tg. The annealing time is preferably 1 minute to 10 hours, more preferably 10 minutes to 1 hour. The annealing atmosphere is preferably a vacuum or inert gas atmosphere.

The organic thin films of the present embodiment have electron transport properties or hole transport properties, and thus can be used in various organic thin film devices such as organic thin film transistors, organic solar cells and optical sensors by controlling transport of electrons or holes injected from electrodes, or charges generated by light absorption. When the organic thin films of the present embodiment are used in such organic thin film devices, the thin films are preferably oriented by orientation treatment and used, because charge transport properties or hole transport properties are further improved.

[Organic Thin Film Device]

The aforementioned organic thin films of the present embodiment comprise the nitrogen-containing compounds of the present embodiment, and thus have high charge (electron or hole) transport properties. Therefore, the organic thin films can efficiently transport electrons or holes injected from electrodes or the like, or charges or the like generated by light absorption, and can be applied to various electrical devices (organic thin film devices) using the organic thin films. The nitrogen-containing compounds of the present embodiment have high environmental stability. Thus, organic thin film devices having stable performance even in a normal atmosphere can be manufactured by forming thin films using them. Examples of the organic thin film devices will be described below, respectively.

(Organic Thin Film Transistor)

First, organic thin film transistors of preferred embodiments will be described. The organic thin film transistors may have a structure comprising a source electrode and a drain electrode; an active layer (i.e., an organic thin film layer) forming a current path between them and containing the nitrogen-containing compound of the present embodiment; and a gate electrode controlling the amount of current passing through the current path, and examples thereof include field effect organic thin film transistors and static induction organic thin film transistors.

The field effect organic thin film transistor preferably comprises a source electrode and a drain electrode; an active layer forming a current path between them and containing the nitrogen-containing compound of the present embodiment; a gate electrode controlling the amount of current passing through the current path; and an insulating layer placed between the active layer and the gate electrode. It is particularly preferred that the source electrode and the drain electrode be provided in contact with the active layer containing the nitrogen-containing compound of the present embodiment and that the gate electrode be provided across the insulating layer in contact with the active layer.

The static induction organic thin film transistor preferably comprises a source electrode and a drain electrode; an active layer forming a current path between them and containing the nitrogen-containing compound of the present embodiment; and a gate electrode controlling the amount of current passing through the current path, the gate electrode provided in the active layer. In particular, the source electrode, the drain electrode, and the gate electrode provided in the active layer are preferably provided in contact with the active layer containing the nitrogen-containing compound of the present embodiment. The structure of the gate electrode is acceptable if the structure can form a path for current flowing from the source electrode to the drain electrode and can control the amount of current flowing in the current path by the voltage applied to the gate electrode; examples thereof include comb-shaped electrodes.

FIG. 1 is a schematic cross-sectional view of an organic thin film transistor (field effect organic thin film transistor) according to a first embodiment. An organic thin film transistor 100 shown in FIG. 1 comprises a substrate 1; a source electrode 5 and a drain electrode 6 formed on the substrate 1 at a predetermined interval between them; an active layer 2 formed on the substrate 1 to cover the source electrode 5 and the drain electrode 6; an insulating layer 3 formed on the active layer 2; and a gate electrode 4 formed on the insulating layer 3 to cover a region of the insulating layer 3 between the source electrode 5 and the drain electrode 6.

Figure 2:
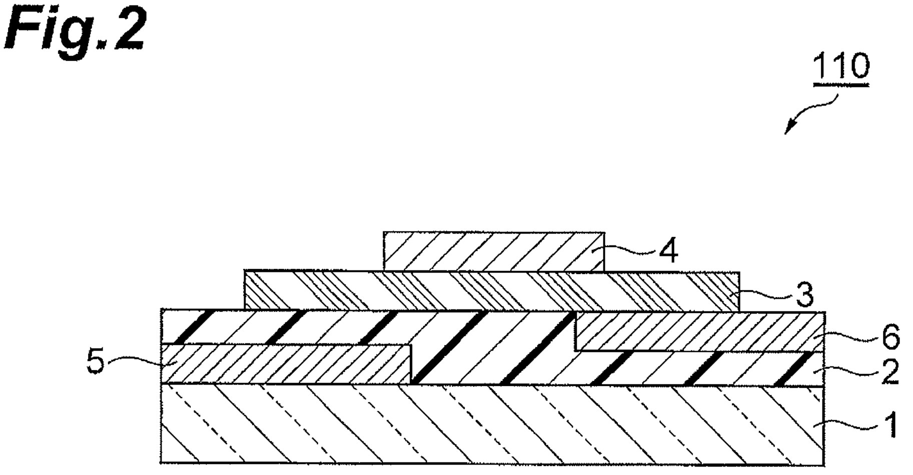
FIG. 2 is a schematic cross-sectional view of an organic thin film transistor according to a second embodiment.

FIG. 2 is a schematic cross-sectional view of an organic thin film transistor (field effect organic thin film transistor) according to a second embodiment. An organic thin film transistor 110 shown in FIG. 2 comprises a substrate 1; a source electrode 5 formed on the substrate 1; an active layer 2 formed on the substrate 1 to cover the source electrode 5; a drain electrode 6 formed on the active layer 2 at a predetermined interval from the source electrode 5; an insulating layer 3 formed on the active layer 2 and the drain electrode 6; and a gate electrode 4 formed on the insulating layer 3 to cover a region of the insulating layer 3 between the source electrode 5 and the drain electrode 6.

Figure 3:
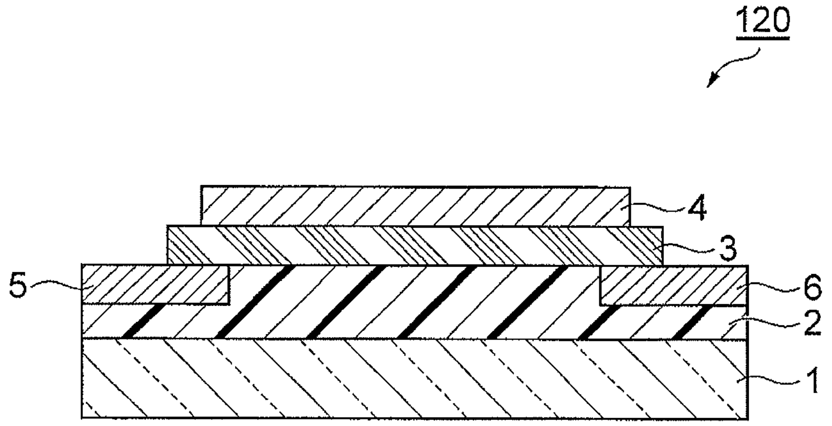
FIG. 3 is a schematic cross-sectional view of an organic thin film transistor according to a third embodiment.

FIG. 3 is a schematic cross-sectional view of an organic thin film transistor (field effect organic thin film transistor) according to a third embodiment. An organic thin film transistor 120 shown in FIG. 3 comprises a substrate 1; an active layer 2 formed on the substrate 1; a source electrode 5 and a drain electrode 6 formed on the active layer 2 at a predetermined interval between them; an insulating layer 3 formed on the active layer 2 to partially cover the source electrode 5 and the drain electrode 6; and a gate electrode 4 formed on the insulating layer 3 to partially cover a region of the insulating layer 3 under which the source electrode 5 is formed and a region of the insulating layer 3 under which the drain electrode 6 is formed, respectively.

Figure 4:
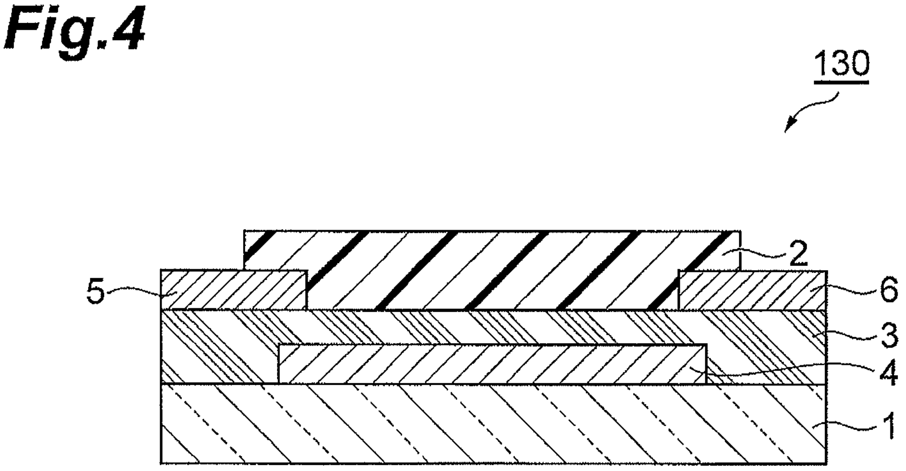
FIG. 4 is a schematic cross-sectional view of an organic thin film transistor according to a fourth embodiment.

FIG. 4 is a schematic cross-sectional view of an organic thin film transistor (field effect organic thin film transistor) according to a fourth embodiment. An organic thin film transistor 130 shown in FIG. 4 comprises a substrate 1; a gate electrode 4 formed on the substrate 1; an insulating layer 3 formed on the substrate 1 to cover the gate electrode 4; a source electrode 5 and a drain electrode 6 formed on the insulating layer 3 at a predetermined interval between them to partially cover a region of the insulating layer 3 under which the gate electrode 4 is formed; and an active layer 2 formed on the insulating layer 3 to partially cover the source electrode 5 and the drain electrode 6.

Figure 5:
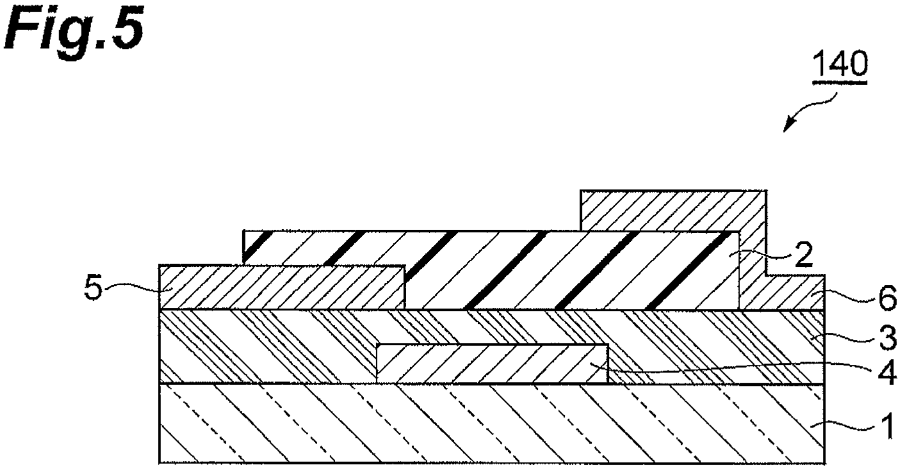
FIG. 5 is a schematic cross-sectional view of an organic thin film transistor according to a fifth embodiment.

FIG. 5 is a schematic cross-sectional view of an organic thin film transistor (field effect organic thin film transistor) according to a fifth embodiment. An organic thin film transistor 140 shown in FIG. 5 comprises a substrate 1; a gate electrode 4 formed on the substrate 1; an insulating layer 3 formed on the substrate 1 to cover the gate electrode 4; a source electrode 5 formed on the insulating layer 3 to partially cover a region of the insulating layer 3 under which the gate electrode 4 is formed; an active layer 2 formed on the insulating layer 3 to partially cover the source electrode 5; and a drain electrode 6 formed on the insulating layer 3 at a predetermined interval from the source electrode 5 to partially cover a region of the active layer 2 under which the gate electrode 4 is formed.

Figure 6:
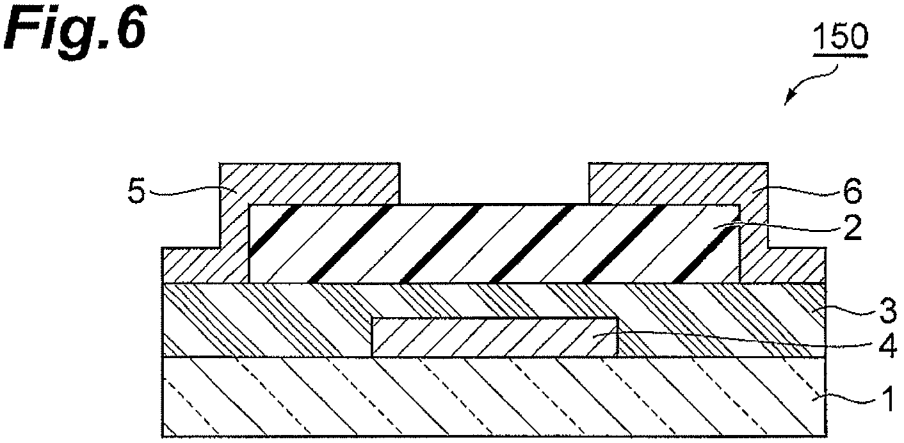
FIG. 6 is a schematic cross-sectional view of an organic thin film transistor according to a sixth embodiment.

FIG. 6 is a schematic cross-sectional view of an organic thin film transistor (field effect organic thin film transistor)

according to a sixth embodiment. An organic thin film transistor 150 shown in FIG. 6 comprises a substrate 1; a gate electrode 4 formed on the substrate 1; an insulating layer 3 formed on the substrate 1 to cover the gate electrode 4; an active layer 2 formed to cover a region of the insulating layer 3 under which the gate electrode 4 is formed; a source electrode 5 formed on the insulating layer 3 to partially cover a region of the active layer 2 under which the gate electrode 4 is formed; and a drain electrode 6 formed on the insulating layer 3 at a predetermined interval from the source electrode 5 to partially cover the region of the active layer 2 under which the gate electrode 4 is formed.

Figure 7:
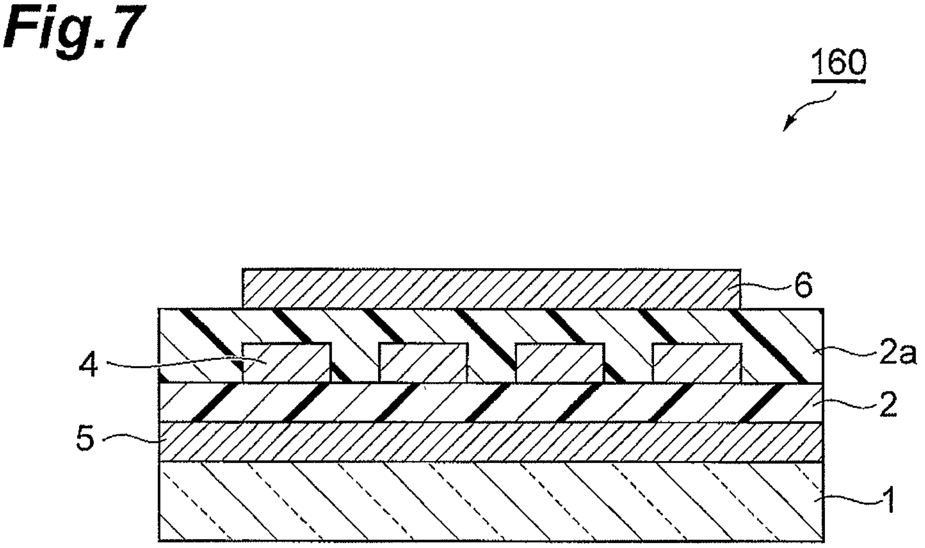
FIG. 7 is a schematic cross-sectional view of an organic thin film transistor according to a seventh embodiment.

FIG. 7 is a schematic cross-sectional view of an organic thin film transistor (static induction organic thin film transistor) according to a seventh embodiment. An organic thin film transistor 160 shown in FIG. 7 comprises a substrate 1; a source electrode 5 formed on the substrate 1; an active layer 2 formed on the source electrode 5; a plurality of gate electrodes 4 formed on the active layer 2 at predetermined intervals between them; an active layer 2*a* formed on the active layer 2 to cover all of the gate electrodes 4 (where the material forming the active layer 2*a* may be identical to or different from that of the active layer 2); and a drain electrode 6 formed on the active layer 2*a*.

In the organic thin film transistors according to the first to seventh embodiments, the active layer 2 and/or the active layer 2*a* contain the nitrogen-containing compound of the present embodiment and form a current path (channel) between the source electrode 5 and the drain electrode 6. The gate electrode 4 controls the amount of current passing through the current path (channel) in the active layer 2 and/or the active layer 2*a* by applying voltage.

Such field effect organic thin film transistors can be produced by known methods, for example, a method described in Japanese Patent Application Laid-Open No. 05-110069. Static induction organic thin film transistors can be produced by known methods, for example, a method described in Japanese Patent Application Laid-Open No. 2004-006476.

The substrate 1 is acceptable if it does not interfere with characteristics as an organic thin film transistor, and glass substrates, flexible film substrates and plastic substrates may be used.

Use of organic solvent-soluble compounds is advantageous and preferable in forming the active layer 2. Thus, the organic thin film to be the active layer 2 can be formed using the method for manufacturing the organic thin films of the present embodiment as described above.

The insulating layer 3 in contact with the active layer 2 is acceptable if it is a material having good electrical insulation properties, and known materials can be used. Examples include SiOx, SiNx, $Ta_2O_5$, polyimide, polyvinyl alcohol, polyvinyl phenol, organic glass and photoresists. Materials having a high dielectric constant are preferred, because this enables low voltage operation.

When the active layer 2 is formed on the insulating layer 3, it is also possible to treat the surface of the insulating layer 3 with a surface treating agent such as a silane coupling agent to improve interface characteristics between the insulating layer 3 and the active layer 2, thereby modifying the surface, and then form the active layer 2. Examples of the surface treating agent include long-chain alkylchlorosilanes, long-chain alkylalkoxysilanes, fluorinated alkylchlorosilanes, fluorinated alkylalkoxysilanes, and silylamine compounds such as hexamethyldisilazane. It is also possible to treat the surface of the insulating layer with ozone UV or $O_2$ plasma before treating with a surface treating agent.

After fabricating the organic thin film transistor, a protective film is preferably formed on the organic thin film transistor to protect the device. This blocks the organic thin film transistor from the atmosphere and can suppress deterioration of characteristics of the organic thin film transistor. The protective film can also reduce the effect from outside in a process of forming a display device driven on the organic thin film transistor.

Examples of the method of forming the protective film include methods of covering with an UV-curable resin, a thermosetting resin or an inorganic SiONx film. In order to effectively block from the atmosphere, the process after the organic thin film transistor is fabricated and before the protective film is formed is preferably performed without exposure to the air (for example, in a dried nitrogen atmosphere or in vacuum).

An organic thin film transistor array can be formed by integrating a plurality of the organic thin film transistors, and can also be used as a backplane for a flat panel display.

Figure 8:
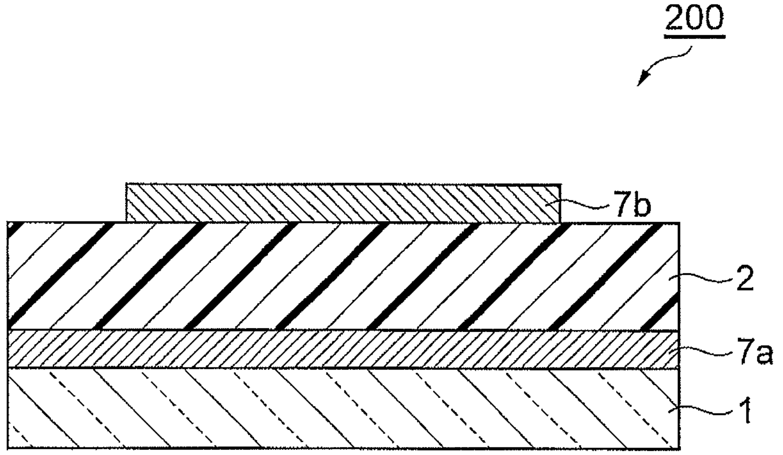
FIG. 8 is a schematic cross-sectional view of a solar cell according to an embodiment.

Next, application of the organic thin films of the present embodiment to solar cells will be described. FIG. 8 is a schematic cross-sectional view of a solar cell according to an embodiment. A solar cell 200 shown in FIG. 8 comprises a substrate 1; a first electrode 7*a* formed on the substrate 1; an active layer 2 formed on the first electrode 7*a* and composed of an organic thin film containing the nitrogen-containing compound of the present embodiment; and a second electrode 7*b* formed on the active layer 2.

In the solar cell of the present embodiment, a transparent or semi-transparent electrode is used for one of the first electrode 7*a* and the second electrode 7*b*. Metals such as aluminum, gold, silver, copper, alkali metals and alkaline earth metals, or their semi-transparent films and transparent conductive films can be used as electrode materials. In order to achieve high open-circuit voltage, the respective electrodes are preferably selected so that the difference between work functions is large. A charge generating agent, a sensitizer or the like can be added to the active layer 2 and used in order to increase photosensitivity. A silicon substrate, a glass substrate, a plastic substrate or the like can be used as the substrate 1.

Figure 9:
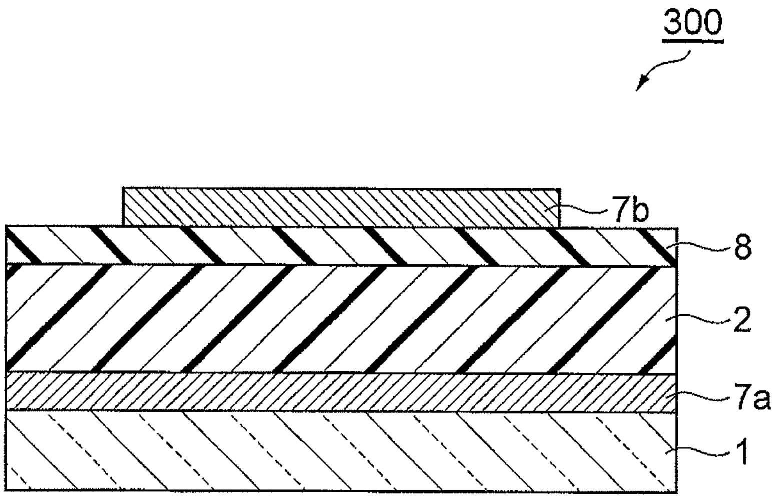
FIG. 9 is a schematic cross-sectional view of an optical sensor according to a first embodiment.

Next, application of the organic thin films of the present embodiment to optical sensors will be described. FIG. 9 is a schematic cross-sectional view of an optical sensor according to a first embodiment. An optical sensor 300 shown in FIG. 9 comprises a substrate 1; a first electrode 7*a* formed on the substrate 1; an active layer 2 formed on the first electrode 7*a* and composed of an organic thin film containing the nitrogen-containing compound of the present embodiment; a charge generating layer 8 formed on the active layer 2; and a second electrode 7*b* formed on the charge generating layer 8.

Figure 10:
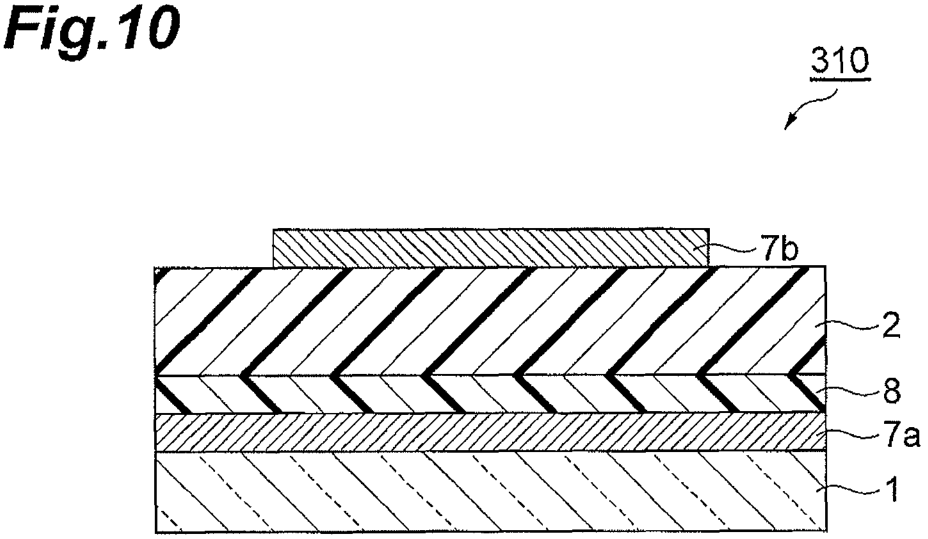
FIG. 10 is a schematic cross-sectional view of an optical sensor according to a second embodiment.

FIG. 10 is a schematic cross-sectional view of an optical sensor according to a second embodiment. An optical sensor 310 shown in FIG. 10 comprises a substrate 1; a first electrode 7*a* formed on the substrate 1; a charge generating layer 8 formed on the first electrode 7*a*; an active layer 2 formed on the charge generating layer 8 and composed of an organic thin film containing the nitrogen-containing compound of the present embodiment; and a second electrode 7*b* formed on the active layer 2.

Figure 11:
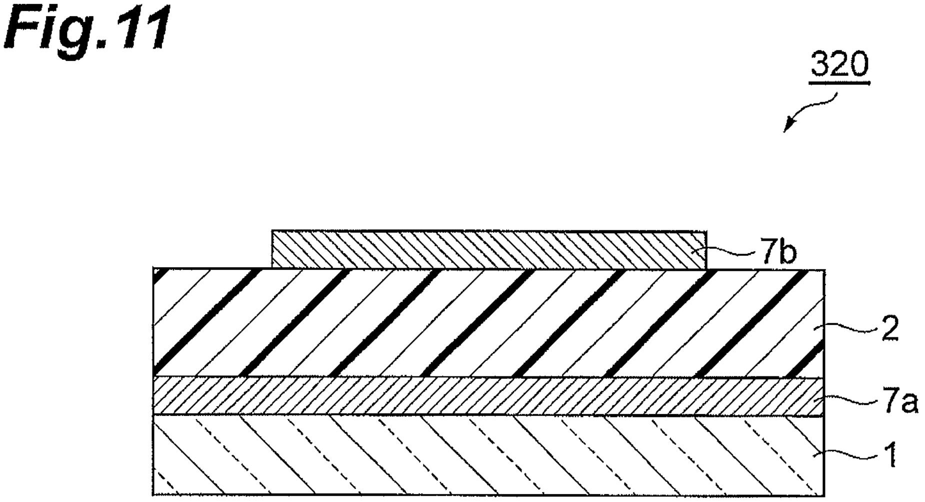
FIG. 11 is a schematic cross-sectional view of an optical sensor according to a third embodiment.

FIG. 11 is a schematic cross-sectional view of an optical sensor according to a third embodiment. An optical sensor 320 shown in FIG. 11 comprises a substrate 1; a first electrode 7*a* formed on the substrate 1; an active layer 2 formed on the first electrode 7*a* and composed of an organic thin film containing the nitrogen-containing compound of the present embodiment; and a second electrode 7*b* formed on the active layer 2.

In the optical sensors of the first to third embodiments, a transparent or semi-transparent electrode is used for one of the first electrode 7*a* and the second electrode 7*b*. The charge generating layer 8 is a layer generating charges by absorbing light. Metals such as aluminum, gold, silver, copper, alkali metals and alkaline earth metals, or their semi-transparent films and transparent conductive films can be used as electrode materials. A carrier generating agent, a sensitizer or the like can be added to the active layer 2 and used in order to increase photosensitivity. A silicon substrate, a glass substrate, a plastic substrate or the like can be used as the substrate 1.

In the foregoing, the present invention has been described in detail based on its embodiments. However, the present invention is not limited to the above embodiments. Various modifications of the present invention are possible without departing from the spirit of the present invention.

EXAMPLES

The present invention will be further described specifically below with reference to Examples and Comparative Examples; however, the present invention is not limited to the following Examples in any way. In the Examples and Comparative Examples, the compounds represented by the formulas (A), (B), (C), (C'), (D), (E), (F), (G), (H), (I), (J), (K), (L), (M), (N), (O), (P), (O), (R), (S), (T), (U), (V), (W), (X), (Y), (Z), (AA), (AB), (AC), (AD), (AE), (AF), (AG), (AH), (AI), (AJ) and (AK) are sequentially called compounds A, B, C, C, D, E, F, G, H, I, J, K, L, M, N, O, P, Q, R, S, T, U, V, W, X, Y, Z, AA, AB, AC, AD, AE, AF, AG, AH, AI, AJ and AK.

(Measurement Conditions)

Nuclear magnetic resonance (NMR) spectra were measured using JMN-270 (trade name) manufactured by JEOL Ltd. ($^1$H measured at 270 MHz). Chemical shifts are expressed as parts per million (ppm). Tetramethylsilane (TMS) was used as internal standard at 0 ppm. Coupling constants (J) are expressed as Hz, and the abbreviations s, d, t, q, m and br represent singlet, doublet, triplet, quartet, multiplet and broad, respectively. Mass spectrometry (MS) measurement was performed by electron ionization (EI) and direct sample introduction (DI) using GCMS-QP5050A (trade name) manufactured by Shimadzu Corporation. Silicagel 60N (trade name) (40 to 50 μm) manufactured by Kanto Chemical Co., Inc. was used as silica gel in column chromatography separation. All chemical substances are reagent-grade and were purchased from Wako Pure Chemical Industries, Ltd., Tokyo Chemical Industry Co., Ltd., Kanto Chemical Co., Inc., Nacalai Tesque, Inc., Sigma-Aldrich Japan K.K. or Daikin Chemical Sales, Ltd. Reaction under microwave irradiation was performed using Initiator™ Ver. 2.5 manufactured by Biotage AB with an output of 400 W at 2.45 GHz.

Cyclic voltammetry (CV) measurement was performed using CV-50W (trade name) manufactured by BAS Inc. as measuring apparatus with a Pt electrode manufactured by BAS Inc. as working electrode, a Pt wire as counter electrode and an Ag wire as reference electrode. During this measurement, the sweep rate was 100 mV/s and the scanning potential region was from −2.8 V to 1.6 V. The reduction potential and the oxidation potential were measured after completely dissolving $1\times10^{-3}$ mol/L of the compound and the polymer and 0.1 mol/L of tetrabutylammonium hexafluorophosphate (TBAPF6) as supporting electrolyte in a monofluorobenzene solvent.

Example 1

Synthesis of Compound A 2,5-Dibromothiophene-3,4-dicarboxylic acid (100 mg, 0.303 mmol), a catalytic amount of DMF and an excess of thionyl chloride were placed in a recovery flask and refluxed for one hour. After the reaction, thionyl chloride was evaporated under vacuum. Next, this was cooled to 0° C., and triethylamine (0.25 mL, 1.818 mmol) was then added and piperidine (0.18 mL, 1.818 mmol) was further added dropwise. After the dropwise addition, the mixture was stirred at room temperature. After three hours, water was added, followed by extraction with chloroform. The organic layer was dried over magnesium sulfate and concentrated under reduced pressure. Purification by silica gel column chromatography (hexane/ethyl acetate=1/1 (volume ratio)) provided a reddish powder compound A (61 mg, yield: 43%). The analysis results and the chemical formula of the resulting compound A are as follows.

TLC $R_f$=0.33 (hexane/ethyl acetate=1/1 (volume ratio))

GC-MS (DI): m/z=464 ($M^+$).

[Chemical Formula 68]

(A)

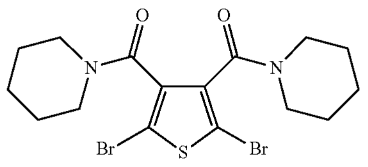

Synthesis of Compound B

The compound A (61 mg, 0.131 mmol), 2-triisopropylsilyl-5-tributyltin-thiazole (153 mg, 0.288 mmol), tetrakis (triphenylphosphine)palladium(0) (15 mg, 0.013 mmol) and toluene (2 mL) were placed in a heated and dried test tube with a cap. The gas in the test tube was replaced with nitrogen, followed by refluxing for eight hours. The reaction solution was filtered through celite and then concentrated under reduced pressure. Purification by silica gel column chromatography (hexane/ethyl acetate=2/1 (volume ratio)) provided a yellow liquid compound B (93 mg, yield: 79%). The analysis results and the chemical formula of the resulting compound B are as follows.

TLC $R_f$=0.32 (hexane/ethyl acetate=2/1 (volume ratio))

$^1$H NMR (400 MHz, $CDCl_3$): δ 8.20 (s, 2H)

GC-MS (DI): m/z=785 ($M^+$).

[Chemical Formula 69]

(B)

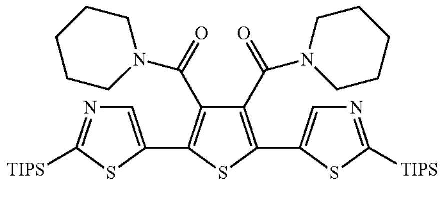

In the formula, TIPS represents a triisopropylsilyl group.

Synthesis of Compound C

The compound B (93 mg, 0.118 mmol) and THF (2 mL) were placed in a heated and dried recovery flask. The gas in the recovery flask was replaced with nitrogen. After cooling to −78° C., lithium diisopropylamide (1 M, 2.6 mL, 1.43 mmol) was added and reacted. After one hour, water was added at −78° C. and the mixture was heated to room temperature, followed by extraction with chloroform. The organic layer was dried over magnesium sulfate and concentrated under reduced pressure. Purification by silica gel column chromatography (hexane/ethyl acetate=10/1 (volume ratio)) provided a purple solid compound C (1 mg, yield: 1.3%). The resulting compound C was soluble in chloroform, ethyl acetate and THF. The analysis results and the chemical formula of the resulting compound C are as follows. TLC $R_f$=0.27 (hexane/ethyl acetate=8/1 (volume ratio))

$^1$H NMR (400 MHz, $CDCl_3$): δ 1.46 (m, 6H), 1.15 (d, 36H)

GC-MS (DI): m/z=614 ($M^+$)

CV measurement was performed for the resulting compound C, and as a result, a reversible reduction wave was observed at −1.29 V, and a reduction in the LUMO level could be confirmed.

[Chemical Formula 70]

(C)

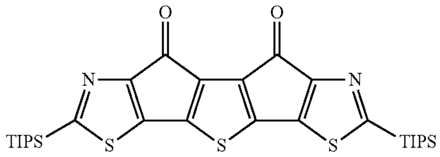

Synthesis of Compound C'

The compound C and THF are placed in a heated and dried recovery flask. The gas in the recovery flask is replaced with nitrogen. After cooling to −78° C., lithium diisopropylamide is added and reacted. After one hour, water is added at −78° C. and the mixture is heated to room temperature, followed by extraction with chloroform. The organic layer is dried over magnesium sulfate and concentrated under reduced pressure. Purification by silica gel column chromatography provides a compound C'.

[Chemical Formula 71]

(C')

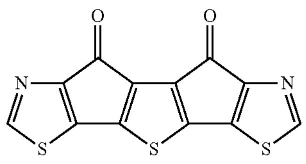

Example 2

Synthesis of Compound D>

1,4-Dibromo-2,5-benzenedicarboxylic acid (10 g, 30.87 mmol), a catalytic amount of DMF and an excess of thionyl chloride were placed in a recovery flask. The gas in the recovery flask was replaced with nitrogen, followed by refluxing for one hour. After the reaction, thionyl chloride was evaporated under vacuum. Next, this was cooled to 0° C., and triethylamine (25.89 mL, 185.2 mmol) was then added and piperidine (18.36 mL, 185.2 mmol) was further added dropwise. After the dropwise addition, the mixture was stirred at room temperature. After two hours, water was added, followed by extraction with dichloromethane. The organic layer was dried over magnesium sulfate and concentrated under reduced pressure. The generated solid was washed with methanol to provide a white solid compound D (11.76 g, yield: 83%). The analysis results and the chemical formula of the resulting compound D are as follows.

$^1$H NMR (400 MHz, $CDCl_3$): δ 7.44 (s, 2H)

GC-MS (DI): m/z=457 ($M^+$).

[Chemical Formula 72]

(D)

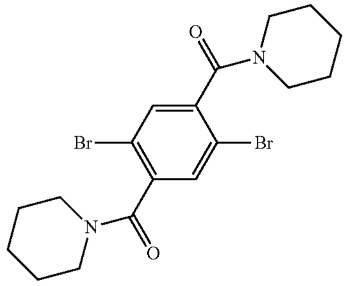

Synthesis of Compound E

The compound D (2 mg, 4.37 mmol), 2-triisopropylsilyl-5-tributyltin-thiazole (5.10 g, 9.60 mmol), tetrakis(triphenylphosphine)palladium(0) (505 mg, 0.44 mmol) and toluene (20 mL) were placed in a heated and dried test tube with a cap. The gas in the test tube was then replaced with nitrogen, followed by refluxing for 10 hours. The reaction solution was filtered through celite and then concentrated under reduced pressure. The generated solid was washed with methanol to provide a white solid compound E (2.65 mg, yield: 78%). The analysis results and the chemical formula of the resulting compound E are as follows.

$^1$H NMR (400 MHz, $CDCl_3$): δ 8.28 (s, 2H), 7.52 (s, 2H)

[Chemical Formula 73]

(E)

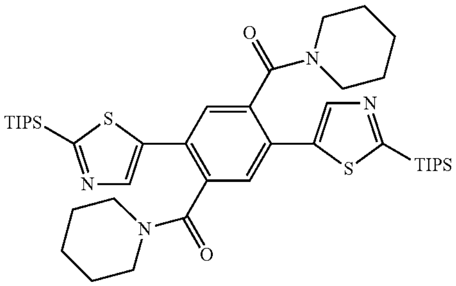

Synthesis of Compound F

The compound E (500 mg, 0.642 mmol) and THF (45 mL) were placed in a heated and dried recovery flask. The gas in the recovery flask was replaced with nitrogen. After cooling to −78° C., lithium diisopropylamide (1 M, 14 mL, 7.77 mmol) was added and reacted. After one hour, water was added at −78° C. and the mixture was heated to room temperature, followed by extraction with chloroform. The organic layer was dried over magnesium sulfate and concentrated under reduced pressure. Purification by silica gel column chromatography (hexane/chloroform=2.5/1 (volume ratio)) provided a purple solid compound F (343 mg, yield: 88%). The resulting compound F was soluble in chloroform, ethyl acetate and THF. The analysis results and the chemical formula of the resulting compound F are as follows.

TLC $R_f$=0.29 (hexane/chloroform=2.5/1 (volume ratio))

GC-MS (DI): m/z=609 ($M^+$).

CV measurement was performed for the resulting compound F, and as a result, a reversible reduction wave was observed at −1.17 V, and a reduction in the LUMO level could be confirmed.

[Chemical Formula 74]

(F)

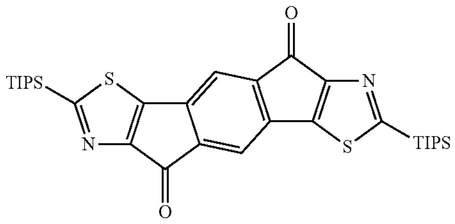

Synthesis of Compound G

The compound F (207 mg, 0.340 mmol) and THF (5 mL) were placed in a heated and dried recovery flask. The gas in the recovery flask was replaced with nitrogen, followed by cooling to 0° C. The mixture was heated to room temperature while a solution of tetrabutylammonium fluoride in THF (1.0 M, 0.850 mL, 0.850 mmol) was added and reacted. After 12 hours, water was added, followed by extraction with chloroform. A green solid suspended in the organic layer was collected by filtration. This was dried under vacuum and purified by sublimation to provide a green solid compound G (74 mg, yield: 74%). The analysis results and the chemical formula of the resulting compound G are as follows.

GC-MS (DI): m/z=296 ($M^+$).

[Chemical Formula 75]

(G)

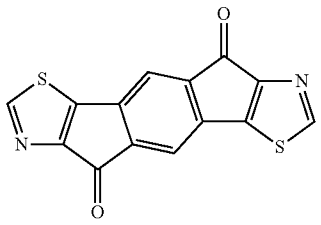

Example 3

Synthesis of Compound H

Thiazole (1 g, 11.75 mmol) and THF (60 mL) were placed in a heated and dried recovery flask. The mixture was cooled to −78° C., and n-butyllithium (8.8 mL, 14.1 mmol) was added and reacted. After 30 minutes, 1-iodohexane (2.74 g, 12.93 mmol) was added. After 30 minutes, the mixture was heated to room temperature. After one hour, water was added, followed by extraction with ethyl acetate. The organic layer was dried over magnesium sulfate and concentrated under reduced pressure. Purification by silica gel column chromatography (hexane/ethyl acetate=10/1 (volume ratio)) provided a brown and transparent compound H (700 mg, yield: 35%). The analysis results and the chemical formula of the resulting compound H are as follows.

TLC $R_f$=0.23 (hexane/ethyl acetate=10/1 (volume ratio))

$^1$H NMR (400 MHz, $CDCl_3$): δ 7.66 (d, 1H), 7.18 (d, 1H), 3.02 (t, 2H), 1.80 (m, 2H), 1.24-1.46 (m, 6H), 0.89 (t, 3H)

[Chemical Formula 76]

(H)

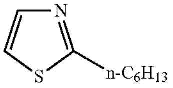

Synthesis of Compound I

The compound H (500 mg, 2.95 mmol) and THF (3 mL) were placed in a heated and dried recovery flask. The mixture was cooled to −78° C., and n-butyllithium (1.9 mL, 3.10 mmol) was added and reacted. After 30 minutes, tributyltin chloride (0.84 mL, 3.10 mmol) was added. After 30 minutes, the mixture was heated to room temperature. After one hour, water was added, followed by extraction with ethyl acetate. The organic layer was dried over magnesium sulfate and concentrated under reduced pressure. Purification by alumina column chromatography (hexane) provided a yellow and transparent compound I (1.15 g, yield: 85%). The analysis results and the chemical formula of the resulting compound I are as follows.

$^1$H NMR (400 MHz, $CDCl_3$): δ 7.58 (s, 1H), 3.06 (t, 2H), 1.81 (m, 2H), 0.90 (m, 12H)

[Chemical Formula 77]

(I)

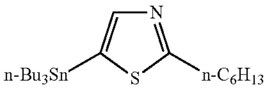

Synthesis of Compound J

The compound D (100 mg, 0.22 mmol), the compound I (220 mg, 0.48 mmol), tetrakis(triphenylphosphine)palladium (0) (25 mg, 0.022 mmol) and toluene (2 mL) were placed in a heated and dried test tube with a cap. The gas in the test tube was then replaced with nitrogen, followed by refluxing for 10 hours. The reaction solution was filtered through celite and then concentrated under reduced pressure. Purification by silica gel column chromatography (hexane/ethyl acetate=1/3 (volume ratio)) provided a compound J (113 mg, yield: 82%). The analysis results and the chemical formula of the resulting compound J are as follows.

TLC $R_f$=0.43 (hexane/ethyl acetate=1:3)

$^1$H NMR (400 MHz, $CDCl_3$): δ 7.80 (s, 1H), 7.45 (s, 1H)

GC-MS (DI): m/z=635 ($M^+$).

[Chemical Formula 78]

(J)

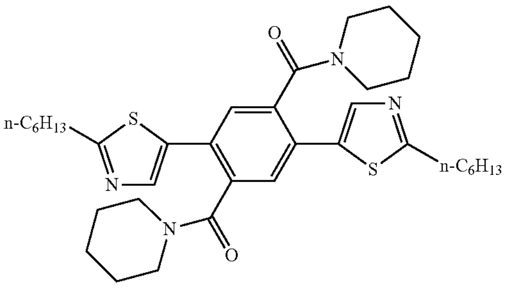

Synthesis of Compound K

The compound J and THF are placed in a heated and dried recovery flask. The gas in the recovery flask is replaced with nitrogen. After cooling to −78° C., lithium diisopropylamide is added and reacted. After one hour, water is added at −78° C. and the mixture is heated to room temperature, followed by extraction with chloroform. The organic layer is dried over magnesium sulfate and concentrated under reduced pressure. Purification by silica gel column chromatography provides a compound K.

[Chemical Formula 79]

(K)

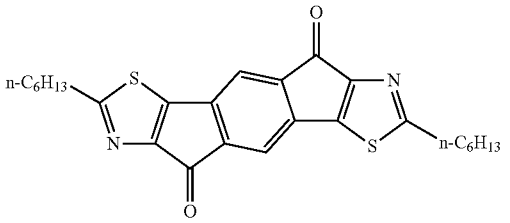

Example 4

Synthesis of Compound L

The compound F (47 mg, 0.077 mmol), 2,2-dibutyl-1,3-propanediol (58 mg, 0.031 mmol), p-toluenesulfonic acid (133 mg, 0.77 mmol) and benzene (30 mL) were placed in a heated and dried recovery flask. The gas in the recovery flask was replaced with nitrogen, followed by refluxing for eight hours. The reaction solution was filtered through celite and then concentrated under reduced pressure. Purification by silica gel column chromatography (hexane/ethyl acetate=20/1 (volume ratio)) provided a compound L (42 mg, 0.066 mmol). The analysis results and the chemical formula of the resulting compound L are as follows.

$^1$H NMR (400 MHz, $CDCl_3$): δ 8.68 (s, 2H), 7.46 (s, 2H), 4.60 (s, 2H), 4.57 (s, 2H), 3.82 (s, 2H), 3.79 (s, 2H).

[Chemical Formula 80]

(L)

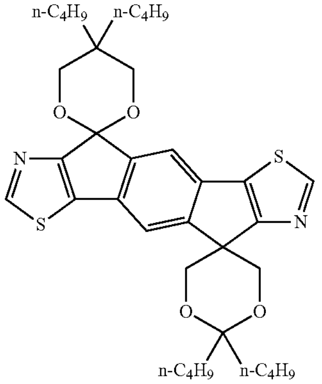

Synthesis of Compound M

The compound L (237 mg, 0.37 mmol) and THF (5 mL) were placed in a heated and dried recovery flask. The gas in the recovery flask was replaced with nitrogen. After cooling to −78° C., n-butyllithium (0.71 mL, 1.12 mmol) was added and reacted. After one hour, tributyltin chloride (0.33 mL, 1.23 mmol) was added at −78° C., followed by heating to room temperature. After one hour, water was added, followed by extraction with ethyl acetate. The organic layer was dried over magnesium sulfate and concentrated under reduced pressure. Purification by alumina column (hexane/deuterated chloroform=10/1 (volume ratio)) provided a compound M (396 mg, yield: 88%). The analysis results and the chemical formula of the resulting compound M are as follows.

$^1$H NMR (400 MHz, $CDCl_3$): δ 7.41 (s, 2H), 4.76 (s, 2H), 4.73 (s, 2H), 3.77 (s, 2H), 3.74 (s, 2H).

[Chemical Formula 81]

(M)

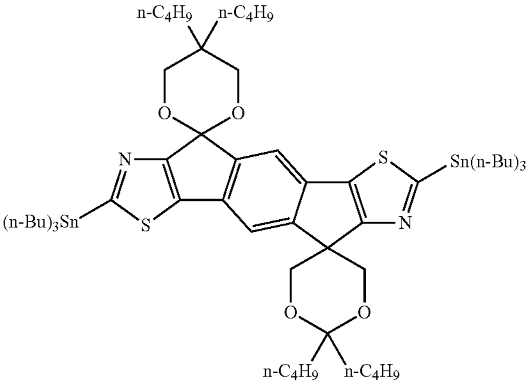

Synthesis of Compound O

The compound M (322 mg, 0.27 mmol), 4'-bromo-2,2,2-trifluoroacetophenone (201 mg, 0.80 mmol), tetrakis(triphenylphosphine)palladium(0) (31 mg, 0.027 mmol) and toluene (3 mL) were placed in a heated and dried test tube with a cap. The gas in the test tube was then replaced with nitrogen, followed by refluxing for 13 hours. The reaction solution was filtered through celite and then concentrated under reduced pressure. The resulting solid was washed with methanol and diethyl ether. The resulting vermilion solid, acetic acid and concentrated hydrochloric acid were placed in a recovery flask and then heated to 100° C. After two hours, the mixture was cooled to room temperature and water was added. The generated solid was washed with water, methanol and diethyl ether. Purification by sublimation under reduced pressure provided a dark green solid compound 0 (77 mg, yield: 45%).

CV measurement was performed for the resulting compound O, and as a result, a reversible reduction wave was observed at −0.88 V, and a reduction in the LUMO level could be confirmed.

[Chemical Formula 82]

(O)

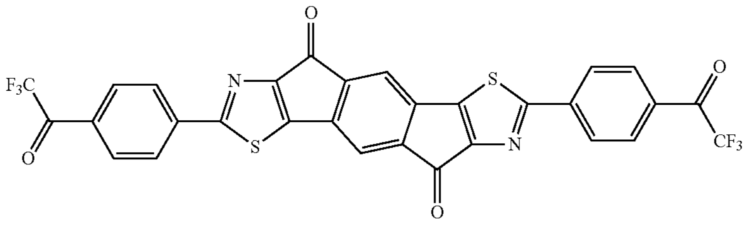

Example 5

Synthesis of Compound P

Thiazole and THF are placed in a heated and dried recovery flask. The gas in the recovery flask is replaced with nitrogen, followed by cooling to −78. n-Butyllithium is added and reacted. After 30 minutes, heptanoyl chloride is added. After 30 minutes, the mixture is heated to room temperature. After one hour, water is added, followed by extraction with ethyl acetate. The organic layer is dried over magnesium sulfate and concentrated under reduced pressure. Purification by silica gel column chromatography provides a compound P.

[Chemical Formula 83]

(P)

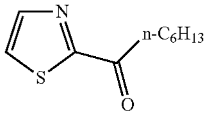

Synthesis of Compound V

The compound P, 2-chloroethanol, DMF and THF are placed in a heated and dried recovery flask. The gas in the recovery flask is replaced with nitrogen, followed by cooling to −78° C. tert-Butoxypotassium is added and reacted. After seven hours, a 10 mass % aqueous ammonium chloride solution is added, followed by extraction with ethyl acetate. The organic layer is dried over magnesium sulfate and concentrated under reduced pressure. Purification by silica gel column chromatography provides a compound V.

[Chemical Formula 84]

(V)

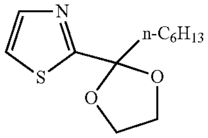

Synthesis of Compound Q

The compound V and THF are placed in a heated and dried recovery flask. The gas in the recovery flask is replaced with nitrogen, followed by cooling to −78° C. n-Butyllithium is then added and reacted. After one hour, tributyltin chloride is added at −78° C. and the mixture is heated to room temperature. After one hour, water is added, followed by extraction with ethyl acetate. The organic layer is dried over magnesium sulfate and concentrated under reduced pressure. Purification by alumina column provides a compound Q.

[Chemical Formula 85]

(Q)

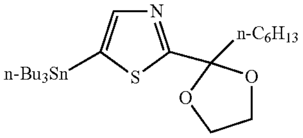

Synthesis of Compound R

The compound D, the compound Q, tetrakis(triphenylphosphine)palladium(0) and toluene are placed in a heated and dried test tube with a cap. The gas in the test tube is then replaced with nitrogen, followed by refluxing for eight hours. The reaction solution is filtered through celite and then concentrated under reduced pressure. Purification by silica gel column chromatography provides a compound R.

[Chemical Formula 86]

(R)

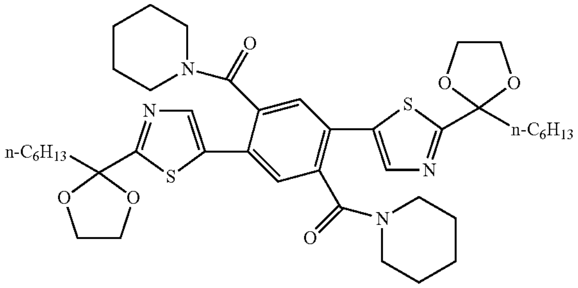

Synthesis of Compound S

The compound R and THF are placed in a heated and dried recovery flask. The gas in the recovery flask is replaced with nitrogen. After cooling to −78° C., lithium diisopropylamide is added and reacted. After one hour, water is added at −78° C. and the mixture is heated to room temperature, followed by extraction with chloroform. The organic layer is dried over magnesium sulfate and concentrated under reduced pressure.

Purification by silica gel column chromatography provides a solid. The resulting solid, acetic acid and concentrated hydrochloric acid are placed in a recovery flask and then heated to 100° C. After two hours, the mixture is cooled to room temperature and water is added. The generated solid is washed with water, methanol and diethyl ether. Purification by sublimation under reduced pressure provides a solid compound S.

[Chemical Formula 87]

(S)

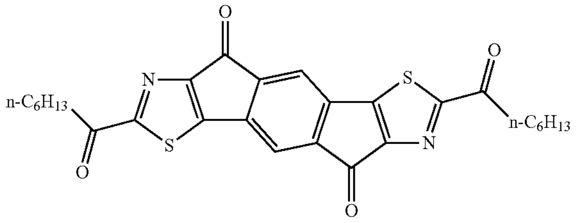

Example 6

Synthesis of Compound T

The compound A, the compound Q, tetrakis(triphenylphosphine)palladium(0) and toluene are placed in a heated and dried test tube with a cap. The gas in the test tube is then replaced with nitrogen, followed by refluxing for eight hours. The reaction solution is filtered through celite and then concentrated under reduced pressure. Purification by silica gel column chromatography provides a compound T.

[Chemical Formula 88]

(T)

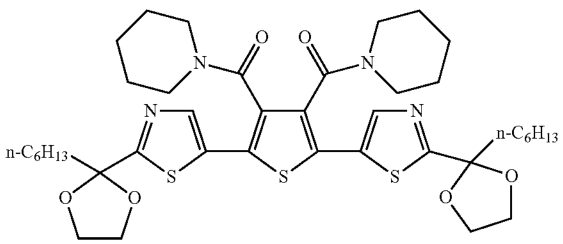

Synthesis of Compound U>

The compound T and THF are placed in a heated and dried recovery flask. The gas in the recovery flask is replaced with nitrogen. After cooling to −78° C., lithium diisopropylamide is added and reacted. After one hour, water is added at −78° C. and the mixture is heated to room temperature, followed by extraction with chloroform. The organic layer is dried over magnesium sulfate and concentrated under reduced pressure. Purification is performed by silica gel column chromatography. The resulting compound, acetic acid and concentrated hydrochloric acid are placed in a recovery flask and then heated to 100° C. After two hours, the mixture is cooled to room temperature and water is added. The generated solid is washed with water, methanol and diethyl ether. Purification by sublimation under reduced pressure provides a solid compound U.

[Chemical Formula 89]

(U)

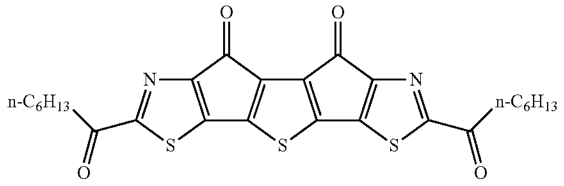

Example 7

Fabrication and Evaluation of Transistor Characteristics of Organic Transistor Device 1

A 300 nm silicon oxide film to be an insulating layer was formed by thermal oxidation on the surface of a heavily doped p-type silicon substrate to be a gate electrode. Source and drain electrodes were formed on the surface of the resulting substrate to prepare a substrate with electrodes. Comb-shaped source and drain electrodes having a channel width of 38 mm and a channel length of 5 μm were formed on the substrate by the lift-off method. The substrate with electrodes was ultrasonically washed with acetone for 10 minutes and then with isopropyl alcohol for 10 minutes, and then irradiated with ozone UV for 30 minutes to wash the substrate surface. An organic thin film of the compound O synthesized in Example 4 was deposited on the washed substrate by vacuum deposition to fabricate an organic transistor device 1. Organic transistor characteristics of the organic transistor device 1 were measured with the gate voltage Vg and the source-drain voltage Vsd changed between 0 and 80 V in vacuum to find good drain current (Id)-gate voltage (Vg) characteristics of an n-type semiconductor. Here, the mobility was 0.27 $cm^2/Vs$, the threshold voltage was 25 V, and the on/off ratio was $10^6$, favorably. Good transistor characteristics were provided even when the organic transistor device 1 was driven in the atmosphere. From this, it was confirmed that the organic transistor device 1 using the compound O effectively functions as an n-type organic transistor, and it was also confirmed that the compound O can be used as an organic n-type semiconductor having high electron transport properties.

Example 8

Synthesis of Compound W

The compound A, the compound tetrakis(triphenylphosphine)palladium(0) and toluene were placed in a heated and dried test tube with a cap. The gas in the test tube was then replaced with nitrogen, followed by refluxing for eight hours. The reaction solution was filtered through celite and then concentrated under reduced pressure. Purification by silica gel column chromatography provided a compound W.

[Chemical Formula 90]

(W)

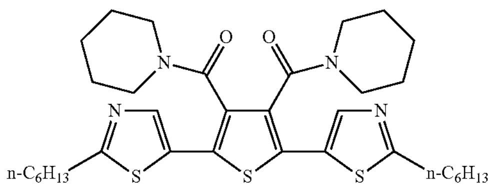

Synthesis of Compound X

The compound W and THF are placed in a heated and dried recovery flask. The gas in the recovery flask is replaced with nitrogen. After cooling to −78° C., lithium diisopropylamide is added and reacted. After one hour, water is added at −78° C. and the mixture is heated to room temperature, followed by extraction with chloroform. The organic layer is dried over magnesium sulfate and concentrated under reduced pressure. Purification by silica gel column chromatography provides a compound X.

[Chemical Formula 91]

(X)

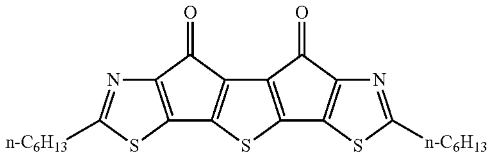

Example 9

Synthesis of Compound Y

The compound M (325 mg, 0.27 mmol), 2-bromo-5-(2',2',2'-trifluoroethanonyl)-thiophene (207 mg, 0.80 mmol), tetrakis(triphenylphosphine)palladium(0) (31 mg, 0.027 mmol) and toluene (3 mL) were placed in a heated and dried test tube with a cap. The gas in the test tube was then replaced with nitrogen, followed by refluxing for 13 hours. The reaction solution was concentrated under reduced pressure, and the resulting solid was washed with methanol and diethyl ether. The resulting red purple solid, acetic acid and concentrated hydrochloric acid were placed in a recovery flask and then heated to 100° C. After 12 hours, the mixture was cooled to room temperature and water was added. The generated solid was washed with water, methanol and diethyl ether. Purification by sublimation under reduced pressure provided a green solid compound Y (25 mg, yield: 14%). The analysis results and the chemical formula of the resulting compound Y are as follows.

MS (TOF): m/z=653.04 ($M^+$)

[Chemical Formula 92]

(Y)

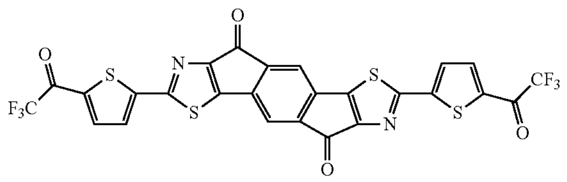

Example 10

Synthesis of Compound Z 1,4-Dibromothiophene-2,5-bismethoxymethylbenzene and THF/tetramethylethylenediamine (10/1 (volume ratio)) were placed in a heated and dried recovery flask, and cooled to −78° C. tert-Butyllithium was added, followed by stirring for one hour. 1-Iodododecane was added, followed by stirring for one hour. Water was then added, followed by extraction with ethyl acetate. The organic layer was dried over magnesium sulfate and concentrated under reduced pressure. Purification by silica gel column chromatography provided a compound Z.

[Chemical Formula 93]

(Z)

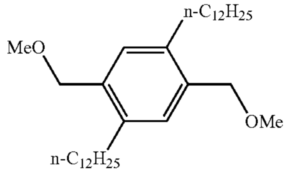

Synthesis of Compound AA

The compound Z, acetic acid and hydrogen bromide were placed in a heated and dried recovery flask, and stirred at room temperature for one hour. Thereafter, water was added, followed by extraction with ethyl acetate. The organic layer was dried over magnesium sulfate and concentrated under reduced pressure. Purification by silica gel column chromatography provided a compound AA.

[Chemical Formula 94]

(AA)

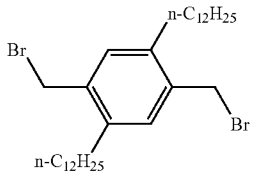

Synthesis of Compound AB

The compound AA, iron, bromine, a catalytic amount of iodine, and dichloromethane were placed in a heated and dried recovery flask, and stirred at 40° C. for 48 hours. Thereafter, the reaction solution was concentrated, washed with diethyl ether and purified to provide a compound AB.

[Chemical Formula 95]

(AB)

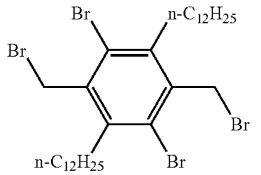

Synthesis of Compound AC

The compound AB (740 mg, 0.97 mmol), dimethyl sulfoxide (DMSO)/chloroform (24 mL/12 mL) and sodium bicarbonate (2.46 g, 29.3 mmol) were placed in a heated and dried recovery flask, and stirred at 100° C. for 12 hours. Thereafter, water was added, followed by extraction with chloroform.

The organic layer was dried over magnesium sulfate and concentrated under reduced pressure. The resulting solid was washed with methanol to provide a compound AC (324 mg, yield: 53%).

[Chemical Formula 96]

(AC)

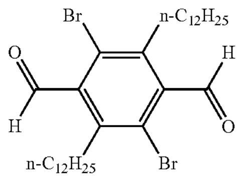

Synthesis of Compound AD

The compound AC (644 mg, 1.02 mmol), sodium dihydrogenphosphate (247 mg, 2.06 mmol), sodium chlorite (188 mg, 1.95 mmol) and DMSO/chloroform/water were placed in a heated and dried recovery flask, and stirred at room temperature for 12 hours. Thereafter, the reaction solution was concentrated under reduced pressure and hydrochloric acid was added, followed by extraction with chloroform. The organic layer was dried over magnesium sulfate and concentrated under reduced pressure to provide a white solid compound AD (470 mg, yield: 70%).

[Chemical Formula 97]

(AD)

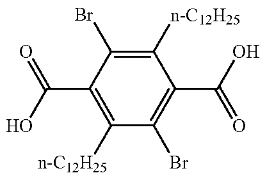

Synthesis of Compound AE

The compound AD (470 mg, 0.71 mmol), a catalytic amount of DMF and an excess of thionyl chloride were placed in a heated and dried recovery flask and refluxed for one hour. After the reaction, thionyl chloride was evaporated under vacuum. Next, dichloromethane was added, followed by cooling to 0° C. Triethylamine (0.4 mL) was then added and piperidine (0.3 mL) was further added dropwise. After the dropwise addition, the mixture was stirred at room temperature. After two hours, water was added, followed by extraction with ethyl acetate. The organic layer was dried over magnesium sulfate and concentrated under reduced pressure. Purification by silica gel column chromatography (hexane/ethyl acetate=5:1) provided a compound AE (240 mg, yield: 42%). The analysis results and the chemical formula of the resulting compound AE are as follows.

$^1$H NMR (400 MHz, $CDCl_3$): δ 3.81 (m), 3.70 (m), 3.15 (m), 2.72 (m), 2.58 (m), 1.80-1.20 (m), 0.89 (t).

[Chemical Formula 98]

(AE)

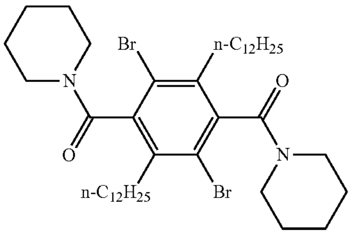

Synthesis of Compound AF

The compound AE (240 mg, 0.30 mmol), 2-triisopropyl-5-trimethyltin-thiazole (366 mg, 0.91 mmol), tetrakis(triphenylphosphine)palladium(0) (4 mg) and toluene (2 mL) were placed in a heated and dried test tube with a cap. The gas in the test tube was replaced with nitrogen, followed by refluxing for 10 hours. The reaction solution was filtered through celite and then concentrated under reduced pressure. Purification by silica gel column chromatography (hexane/ethyl acetate=6/1 (volume ratio)) provided a compound AF (90 mg, yield: 27%).

[Chemical Formula 99]

(AF)

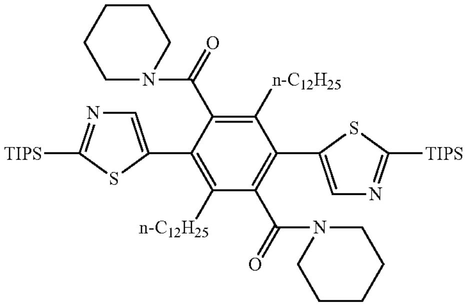

Synthesis of Compound AG

The compound AF (333 mg, 0.29 mmol) and THF (10 mL) were placed in a heated and dried recovery flask. The gas in the recovery flask was replaced with nitrogen. After cooling to −78° C., lithium diisopropylamide (1 M) was added and reacted. After one hour, water was added at −78° C. and the mixture was heated to room temperature, followed by extraction with chloroform. The organic layer was dried over magnesium sulfate and concentrated under reduced pressure. Purification by silica gel column chromatography (hexane/ethyl acetate=60/1 (volume ratio)) provided a compound AG (52 mg, yield: 18%). The analysis results and the chemical formula of the resulting compound AG are as follows.

$^1$H NMR (400 MHz, $CDCl_3$): δ 3.05 (t, 4H), 1.62-1.06 (m), 0.88 (t, 6H).

[Chemical Formula 100]

(AG)

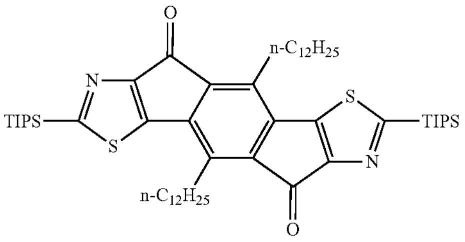

Synthesis of Compound AH

The compound AG (30 mg, 0.032 mmol), 2,2-dibutyl-1,3-propanediol (36 mg, 0.192 mmol), p-toluenesulfonic acid (55 mg, 0.32 mmol) and benzene (2 mL) were placed in a heated and dried recovery flask. The gas in the recovery flask was replaced with nitrogen, followed by refluxing for 24 hours. After leaving to cool, water was added, followed by extraction with ethyl acetate. The organic layer was dried over magnesium sulfate and concentrated under reduced pressure. Purification by silica gel column chromatography (hexane/ethyl acetate=5/1 (volume ratio)) provided a compound AH (11 mg, yield: 35%). The analysis results and the chemical formula of the resulting compound AH are as follows.

TLC $R_f$=0.65 (hexane/ethyl acetate=5:1 (volume ratio))

$^1$H NMR (400 MHz, $CDCl_3$): δ 8.68 (s, 2H), 4.71 (d, J=11.5 Hz, 4H), 3.78 (d, J=11.5 Hz, 4H), 3.10 (m, 4H), 1.98 (m, 4H), 1.7-1.2 (m), 1.01 (t, J=7.1 Hz, 6H), 0.94 (t, J=7.1 Hz, 6H), 0.88 (t, J=6.8 Hz, 6H)

MS (MALDI): m/z=970.18 ($M^+$).

[Chemical Formula 101]

(AH)

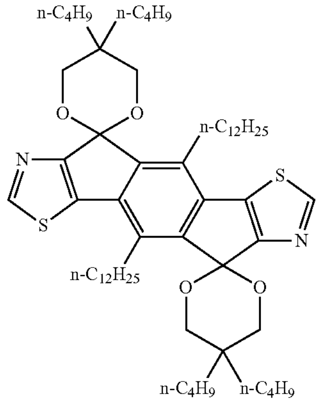

Synthesis of Compound AI

The compound AH and THF are placed in a heated and dried recovery flask. The gas in the recovery flask is replaced with nitrogen, followed by cooling to −78° C. n-Butyllithium is then added and reacted. After one hour, tributyltin chloride is added at −78° C. and the mixture is heated to room temperature. After one hour, water is added, followed by extraction with ethyl acetate. The organic layer is dried over magnesium sulfate and concentrated under reduced pressure. Purification by alumina column provides a compound AI.

[Chemical Formula 102]

(AI)

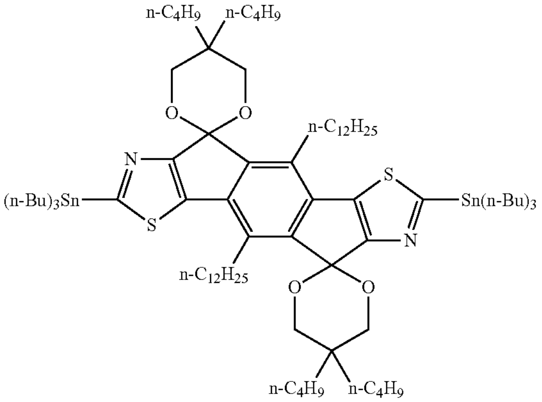

Synthesis of Compound AJ

The compound AI, 4'-bromo-2,2,2-trifluoroacetophenone, tetrakis(triphenylphosphine)palladium(0) and toluene are placed in a heated and dried test tube with a cap. The gas in the test tube is then replaced with nitrogen, followed by refluxing for 13 hours. The reaction solution is filtered through celite and then concentrated under reduced pressure. The resulting solid is washed with methanol and diethyl ether. The resulting solid, acetic acid and concentrated hydrochloric acid are placed in a recovery flask and then heated to 100° C. After two hours, the mixture is cooled to room temperature and water is added. The generated solid is washed with water, methanol and diethyl ether. Purification by sublimation under reduced pressure provides a compound AJ.

[Chemcial Formula 103]

(AJ)

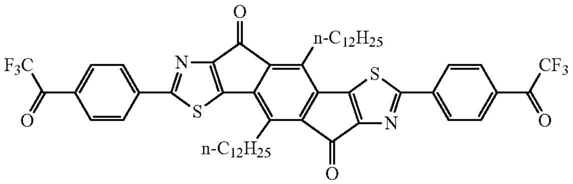

Example 11

Synthesis of Compound AK

The compound AI, 2-bromo-5-(2',2',2'-trifluoroethanonyl)-thiophene, tetrakis(triphenylphosphine)palladium(0) and toluene are placed in a heated and dried test tube with a cap. The gas in the test tube is then replaced with nitrogen, followed by refluxing for 13 hours. The reaction solution is filtered through celite and then concentrated under reduced pressure. The resulting solid is washed with methanol and diethyl ether. The resulting solid, acetic acid and concentrated hydrochloric acid are placed in a recovery flask and then heated to 100° C. After two hours, the mixture is cooled to room temperature and water is added. The generated solid is washed with water, methanol and diethyl ether. Purification by sublimation under reduced pressure provides a compound AK.

[Chemcial Formula 104]

(AK)

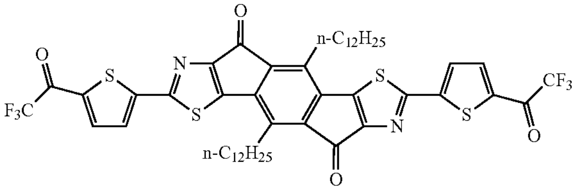

Example 12

Fabrication and Evaluation of Transistor Characteristics of Organic Transistor Device 2

An organic transistor device 2 was fabricated in the same manner as in Example 7 except for using the compound Y of Example 9 in place of the compound 0.

Organic transistor characteristics of the resulting organic transistor device 2 were measured with the gate voltage Vg and the source-drain voltage Vsd changed between 0 and 80 V in vacuum to find good Id-Vg characteristics of an n-type semiconductor. Here, the mobility was 0.17 $cm^2/Vs$, the threshold voltage was 15 V, and the on/off ratio was $10^4$, favorably. Good transistor characteristics were provided even when the organic transistor device 2 was driven in the atmosphere.

Figure 12:
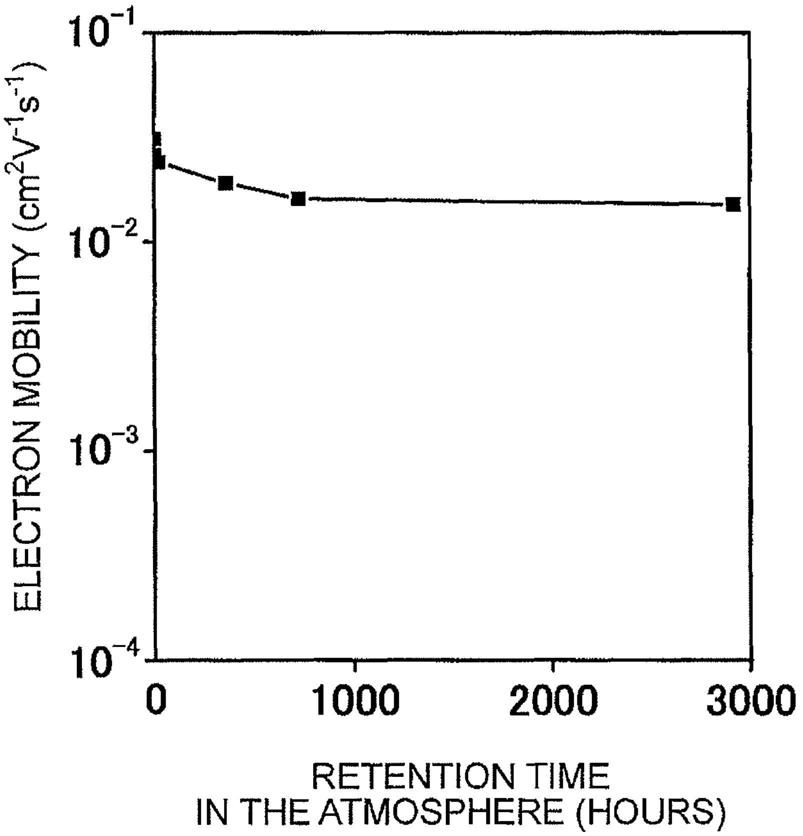
FIG. 12 is a graph showing organic transistor characteristics when an organic transistor device 2 fabricated in Example 12 was maintained in the atmosphere.

FIG. 12 is a graph showing organic transistor characteristics when the organic transistor device 2 was stored in the atmosphere. Characteristics of the organic transistor device 2 after storage in the atmosphere were measured to find that the electron mobility was not considerably reduced even after 3000 hours, as shown in FIG. 12. From this, it was confirmed that the organic transistor device 2 using the compound Y effectively functions as an n-type organic transistor and also has high stability in the atmosphere. It was also confirmed that the compound Y can be used as an organic n-type semiconductor having high electron transport properties.

Comparative Example 1

Synthesis of Compound AL

A compound AL was synthesized by the method described in Japanese Patent Application Laid-Open No. 2009-21527. The target compound obtained by the synthesis was poorly soluble in organic solvents. The resulting synthesized compound was purified by sublimation under reduced pressure to provide a green solid of the compound AL (33 mg, yield: 21%). The analysis results and the chemical formula of the resulting compound AL are as follows.

$^1H$ NMR (400 MHz, $CDCl_3$): δ 8.08 (d, 4H, J=8.8 Hz), 8.05 (d, 4H, J=8.8 Hz)

GC-MS (DI): m/z=538 ($M^+$)

[Chemical Formula 105]

(AL)

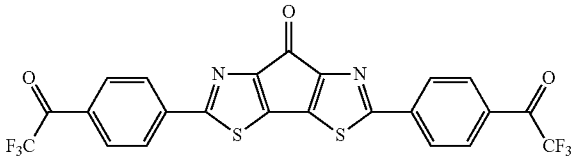

Fabrication and Evaluation of Transistor Characteristics of Organic Transistor Device 3

A washed substrate having source and drain electrodes formed was prepared in the same manner as in Example 7. An organic thin film of the compound AL synthesized above was formed thereon by vacuum deposition at a substrate temperature of 110° C. and a deposition rate of 0.2 nm/min to fabricate an organic transistor device 3. Organic transistor characteristics of the organic transistor device 3 were measured with the gate voltage Vg changed between 0 and 120 V and the source-drain voltage Vsd changed between 0 and 100 V in vacuum to find Id-Vg characteristics of an n-type semiconductor. Here, the mobility was $5.6\times10^{-2}$ $cm^2/Vs$, the threshold voltage was 20 V, and the on/off ratio was $10^6$.

| Reference Signs List | |
|---|---|
| 1 | Substrate |
| 2 | Active layer |
| 2a | Active layer |
| 3 | Insulating layer |
| 4 | Gate electrode |
| 5 | Source electrode |
| 6 | Drain electrode |
| 7a | First electrode |
| 7b | Second electrode |
| 8 | Charge generating layer |
| 100 | Organic thin film transistor according to a first embodiment |
| 110 | Organic thin film transistor according to a second embodiment |
| 120 | Organic thin film transistor according to a third embodiment |
| 130 | Organic thin film transistor according to a fourth embodiment |
| 140 | Organic thin film transistor according to a fifth embodiment |
| 150 | Organic thin film transistor according to a sixth embodiment |
| 160 | Organic thin film transistor according to a seventh embodiment |
| 200 | Solar cell according to an embodiment |
| 300 | Optical sensor according to a first embodiment |
| 310 | Optical sensor according to a second embodiment |
| 320 | Optical sensor according to a third embodiment |

The invention claimed is:

1. A nitrogen-containing fused ring compound having at least one structural unit selected from the group consisting of a structural unit represented by the formula (1-1) and a structural unit represented by the formula (1-2):

[Chemcial Formula 1]

(1-1)

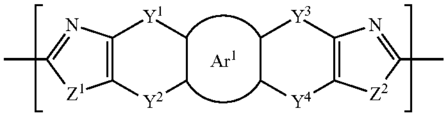

-continued (1-2)

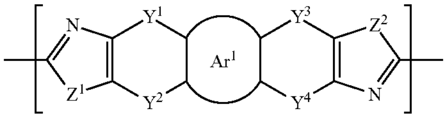

wherein $Ar^1$ represents an aromatic ring having 4 or more carbon atoms which may have a substituent, either one of $Y^1$ and $Y^2$ represents a group represented by —C(=$X^1$)— and the other represents a single bond, either one of $Y^3$ and $Y^4$ represents a group represented by —C(=$X^2$)— and the other represents a single bond, $X^1$ and $X^2$ each independently represent an oxygen atom, a sulfur atom or a group represented by =C($A^1$)$_2$ (wherein $A^1$ represents a hydrogen atom, a halogen atom or a monovalent group, and two $A^1$s may be identical to or different from each other), and $Z^1$ and $Z^2$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5):

[Chemical Formula 2]

(a-1)

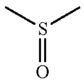

(a-2)

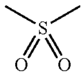

(a-3)

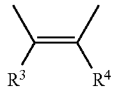

(a-4)

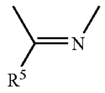

(a-5)

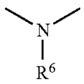

wherein $R^3$, $R^4$, $R^5$ and $R^6$ each independently represent a hydrogen atom, a halogen atom or a monovalent group, and $R^3$ and $R^4$ may be bonded to each other to form a ring.

2. The nitrogen-containing fused ring compound according to claim 1, wherein $Z^1$ and $Z^2$ are sulfur atoms.

3. The nitrogen-containing fused ring compound according to claim 1, wherein $X^1$ and $X^2$ are oxygen atoms.

4. The nitrogen-containing fused ring compound according to claim 1, wherein $Ar^1$ is a benzene ring or a thiophene ring.

5. The nitrogen-containing fused ring compound according to claim 1, wherein the structural unit represented by the formula (1-1) is a structural unit represented by the formula (2-1), and the structural unit represented by the formula (1-2) is a structural unit represented by the formula (2-2):

[Chemical Formula 3]

(2-1)

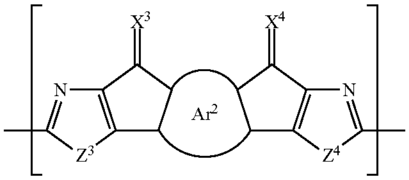

(2-2)

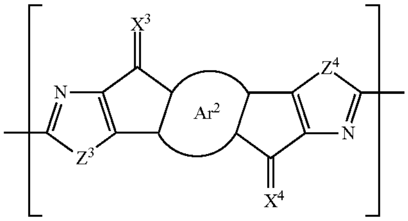

wherein $Ar^2$ represents an aromatic ring having 4 or more carbon atoms which may have a substituent, $X^3$ and $X^4$ each independently represent an oxygen atom, a sulfur atom or a group represented by =C($A^2$)$_2$ (wherein $A^2$ represents a hydrogen atom, a halogen atom or a monovalent group, and two $A^2$s may be identical to or different from each other, provided that at least one of the two $A^2$s represents a cyano group, a nitro group, an acyl group, an alkoxycarbonyl group, a carboxyl group, a hydroxy group or a halogen atom), and $Z^3$ and $Z^4$ each independently represent an oxygen atom, a sulfur atom, a selenium atom, a tellurium atom, a group represented by the formula (b-1), a group represented by the formula (b-2), a group represented by the formula (b-3), a group represented by the formula (b-4) or a group represented by the formula (b-5):

[Chemical Formula 4]

(b-1)

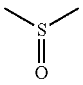

(b-2)

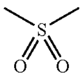

(b-3)

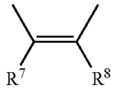

(b-4)

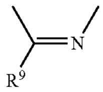

(b-5)

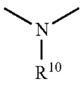

wherein $R^7$, $R^8$, $R^9$ and $R^{10}$ each independently represent a hydrogen atom, a halogen atom or a monovalent group, and $R^7$ and $R^8$ may be bonded to each other to form a ring.

6. The nitrogen-containing fused ring compound according to claim 5, wherein $Z^3$ and $Z^4$ are sulfur atoms.

7. The nitrogen-containing fused ring compound according to claim 5, wherein $X^3$ and $X^4$ are oxygen atoms.

8. The nitrogen-containing fused ring compound according to claim 5, wherein $Ar^2$ is a benzene ring or a thiophene ring.

9. The nitrogen-containing fused ring compound according to claim 1, wherein the structural unit represented by the formula (1-1) is a structural unit represented by the formula (3-1), and the structural unit represented by the formula (1-2) is a structural unit represented by the formula (3-2):

[Chemical Formula 5]

(3-1)

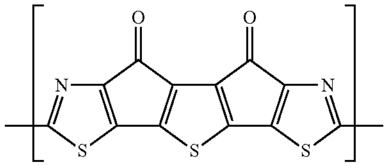

(3-2)

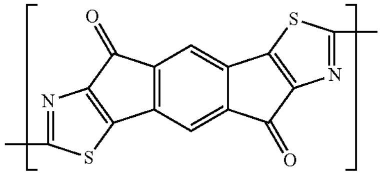

10. A nitrogen-containing fused ring polymer having a plurality of structural units (where the plurality of structural units may be identical to or different from each other) selected from the group consisting of structural units represented by the formula (1-1) and structural units represented by the formula (1-2):

[Chemical Formula 6]

(1-1)

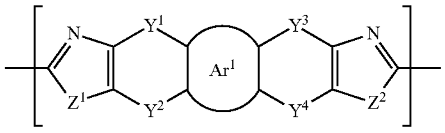

(1-2)

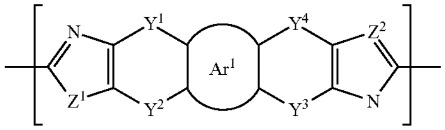

wherein $Ar^1$ represents an aromatic ring having 4 or more carbon atoms which may have a substituent, either one of $Y^1$ and $Y^2$ represents a group represented by $—C(═X^1)—$ and the other represents a single bond, either one of $Y^3$ and $Y^4$ represents a group represented by $—C(═X^2)—$ and the other represents a single bond, $X^1$ and $X^2$ each independently represent an oxygen atom, a sulfur atom or a group represented by $═C(A^1)_2$ (wherein $A^1$ represents a hydrogen atom, a halogen atom or a monovalent group, and two $A^1$s may be identical to or different from each other), and $Z^1$ and $Z^2$ each independently represent an oxygen atom, a sulfur atom, a selenium atom, a tellurium atom, a group represented by the formula (a-1), a group represented by the formula (a-2), a group represented by the formula (a-3), a group represented by the formula (a-4) or a group represented by the formula (a-5):

[Chemical Formula 7]

(a-1)

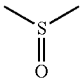

(a-2)

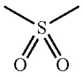

(a-3)

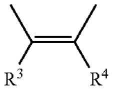

(a-4)

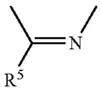

(a-5)

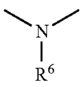

wherein $R^3$, $R^4$, $R^5$ and $R^6$ each independently represent a hydrogen atom, a halogen atom or a monovalent group, and $R^3$ and $R^4$ may be bonded to each other to form a ring.

11. The nitrogen-containing fused ring polymer according to claim 10, wherein $Z^1$ and $Z^2$ are sulfur atoms.

12. The nitrogen-containing fused ring polymer according to claim 10, wherein $X^1$ and $X^2$ are oxygen atoms.

13. The nitrogen-containing fused ring polymer according to claim 10, wherein $Ar^1$ is a benzene ring or a thiophene ring.

14. The nitrogen-containing fused ring polymer according to claim 10, wherein the structural unit represented by the formula (1-1) is a structural unit represented by the formula (2-1), and the structural unit represented by the formula (1-2) is a structural unit represented by the formula (2-2):

[Chemical Formula 8]

(2-1)

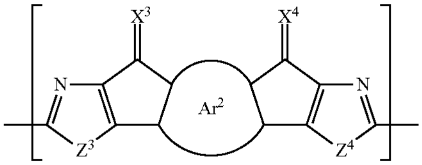

(2-2)

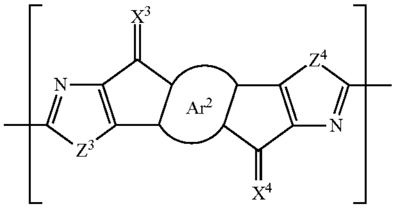

wherein $Ar^2$ represents an aromatic ring having 4 or more carbon atoms which may have a substituent, $X^3$ and $X^4$ each independently represent an oxygen atom, a sulfur atom or a group represented by $=C(A^2)_2$ (wherein $A^2$ represents a hydrogen atom, a halogen atom or a monovalent group, and two $A^2$s may be identical to or different from each other, provided that at least one of the two $A^2$s represents a cyano group, a nitro group, an acyl group, an alkoxycarbonyl group, a carboxyl group, a hydroxy group or a halogen atom), and $Z^3$ and $Z^4$ each independently represent an oxygen atom, a sulfur atom, a selenium atom, a tellurium atom, a group represented by the formula (b-1), a group represented by the formula (b-2), a group represented by the formula (b-3), a group represented by the formula (b-4) or a group represented by the formula (b-5):

[Chemical Formula 9]

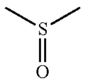
(b-1)

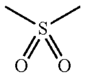
(b-2)

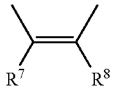
(b-3)

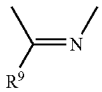
(b-4)

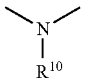
(b-5)

wherein $R^7$, $R^8$, $R^9$ and $R^{10}$ each independently represent a hydrogen atom, a halogen atom or a monovalent group, and $R^7$ and $R^8$ may be bonded to each other to form a ring.

15. The nitrogen-containing fused ring polymer according to claim 14, wherein $Z^3$ and $Z^4$ are sulfur atoms.

16. The nitrogen-containing fused ring polymer according to claim 14, wherein $X^3$ and $X^4$ are oxygen atoms.

17. The nitrogen-containing fused ring polymer according to claim 14, wherein $Ar^2$ is a benzene ring or a thiophene ring.

18. The nitrogen-containing fused ring polymer according to claim 10, further having a structural unit represented by the formula (4):

[Chemical Formula 10]

$$-(Ar^3)- \quad (4)$$

wherein $Ar^3$ represents an arylene group which may have a substituent, or a heterocyclic group which may have a substituent.

19. The nitrogen-containing fused ring polymer according to claim 10, further having a structural unit represented by the formula (5):

[Chemical Formula 11]

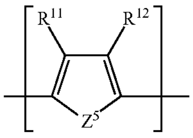
(5)

wherein $R^{11}$ and $R^{12}$ each independently represent a hydrogen atom, a halogen atom or a monovalent group, and $Z^5$ represents an oxygen atom, a sulfur atom, a selenium atom, a tellurium atom, a group represented by the formula (c-1), a group represented by the formula (c-2), a group represented by the formula (c-3), a group represented by the formula (c-4) or a group represented by the formula (c-5):

[Chemical Formula 12]

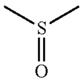
(c-1)

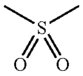
(c-2)

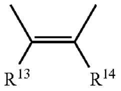
(c-3)

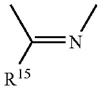
(c-4)

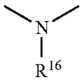
(c-5)

wherein $R^{13}$, $R^{14}$, $R^{15}$ and $R^{16}$ each independently represent a hydrogen atom, a halogen atom or a monovalent group, and $R^{13}$ and $R^{14}$ may be bonded to each other to form a ring.

20. The nitrogen-containing fused ring polymer according to claim 19, wherein $Z^5$ is a sulfur atom.

21. An organic thin film comprising the nitrogen-containing fused ring compound according to claim 1.

22. An organic thin film device comprising the organic thin film according to claim 21.

23. An organic thin film transistor comprising the organic thin film according to claim 21.

24. An organic solar cell comprising the organic thin film according to claim 21.

25. An organic thin film comprising the nitrogen-containing fused ring polymer according to claim 10.

26. An organic thin film device comprising the organic thin film according to claim 25.

27. An organic thin film transistor comprising the organic thin film according to claim 25.

28. An organic solar cell comprising the organic thin film according to claim 25.

* * * * *